United States Patent [19]
Nord

[11] Patent Number: 5,823,771
[45] Date of Patent: Oct. 20, 1998

[54] VERTICAL STRAIGHT WIRE ORTHODONTIC APLLIANCE HAVING INTERCHANGEABLE ANCHOR COMPONENTS

[76] Inventor: Philip J. Nord, 840 Section Line Ave., Seaside, Oreg. 97138

[21] Appl. No.: 863,484

[22] Filed: May 27, 1997

[51] Int. Cl.⁶ .................................................. A61C 7/00
[52] U.S. Cl. .................................................. 433/14; 433/8
[58] Field of Search ................................ 433/8, 9, 10, 11, 433/12, 13, 14, 16, 17

[56] References Cited

U.S. PATENT DOCUMENTS

| | | | |
|---|---|---|---|
| 1,280,628 | 10/1918 | Angle | 433/14 |
| 2,378,279 | 6/1945 | Begg . | |
| 2,686,365 | 8/1954 | Schurter | 433/14 |
| 3,085,335 | 4/1963 | Kesling | 433/14 |
| 3,163,933 | 1/1965 | Begg et al. . | |
| 3,262,207 | 7/1966 | Kesling | 433/10 |
| 3,416,229 | 12/1968 | Kesling | 433/13 |
| 3,423,833 | 1/1969 | Pearlman . | |
| 3,521,355 | 7/1970 | Pearlman . | |
| 3,660,900 | 5/1972 | Andrews . | |
| 3,772,787 | 11/1973 | Hanson | 433/14 |
| 3,793,730 | 2/1974 | Begg et al. . | |
| 4,134,208 | 1/1979 | Pearlman . | |
| 4,249,898 | 2/1981 | Andrews | 433/21 |
| 4,427,381 | 1/1984 | Hall | 433/14 |
| 4,496,318 | 1/1985 | Connelly, Jr. | 433/14 |
| 4,664,626 | 5/1987 | Kesling | 433/14 |
| 4,674,978 | 6/1987 | Acevedo | 433/8 |
| 4,797,095 | 1/1989 | Armstrong et al. | 433/22 |
| 4,917,602 | 4/1990 | Broussard | 433/8 |
| 5,248,257 | 9/1993 | Cannon | 433/14 |
| 5,362,233 | 11/1994 | Thompson | 433/9 |
| 5,613,850 | 3/1997 | Wildman et al. | 433/14 |

FOREIGN PATENT DOCUMENTS

| | | | |
|---|---|---|---|
| 2497657 | 7/1982 | France | 433/8 |

*Primary Examiner*—Ralph A. Lewis
*Attorney, Agent, or Firm*—Kolisch, Hartwell, Dickinson, McCormack & Heuser

[57] ABSTRACT

An orthodontic bracket in two parts includes firstly a base adapted for adhesion to a front of a tooth and including an elongate aperture therethrough, and secondly an elongate, undulated anchor sized for placement by a force fit within the elongate aperture of the base. On opposite ends of the anchor are respectively placed a head having a wire slot that is open on one side passing transversely therethrough, and a lip oriented in the direction of the open side of the bracket and adapted to extend outwardly from the elongate aperture towards the tooth when the anchor is placed within the aperture. The head may have various torque angles so as to provide varying degrees of torque to a tooth upon which applied.

A second embodiment of the anchor includes an anchor post having bilateral extensions therefrom for purposes of causing tooth rotation; a third embodiment of the invention includes pairs of anchor posts disposed at opposite ends of the anchor as secondary means for interconnection between teeth either laterally within an arch or vertically between arches; a fourth embodiment of the invention provides means for installing a tipping spring therein; and a fifth embodiment of the invention provides slots at opposite ends of the anchor that lie in the labial-lingual direction as secondary means for bilateral interconnection from a particular tooth to facing teeth on either or both sides thereof.

11 Claims, 18 Drawing Sheets

Fig. 4b
Fig. 4a
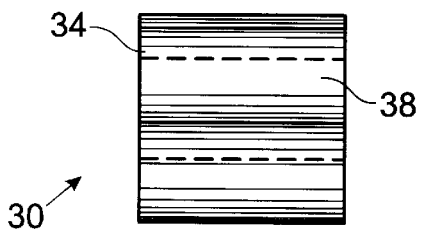
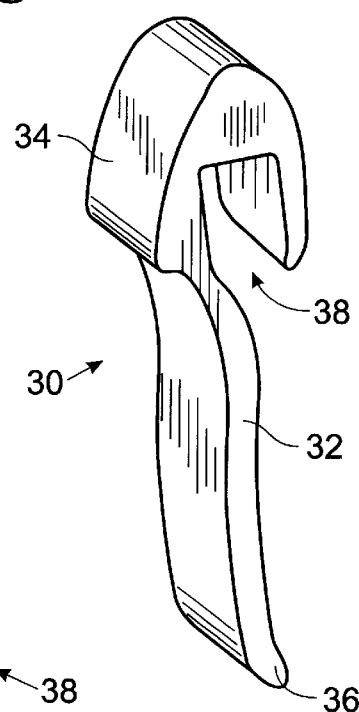
Fig. 4c
Fig. 4d
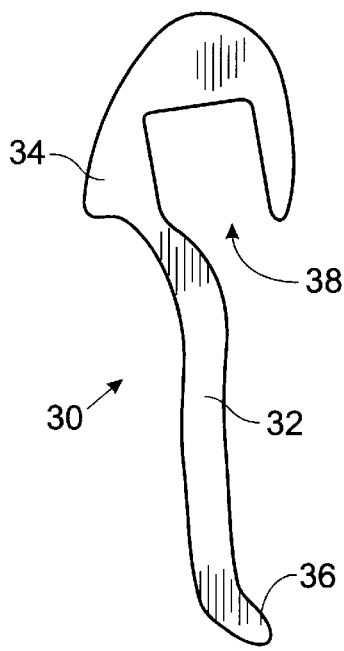
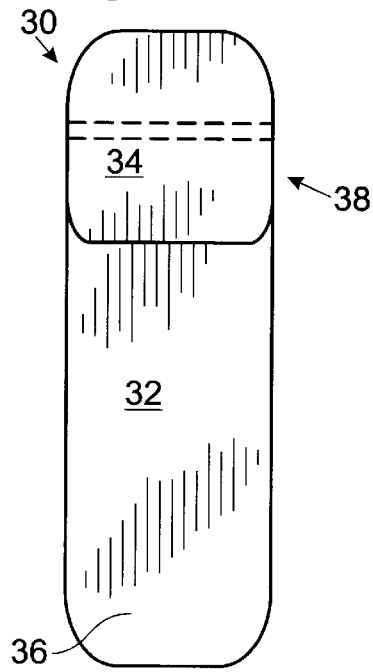
Fig. 4f
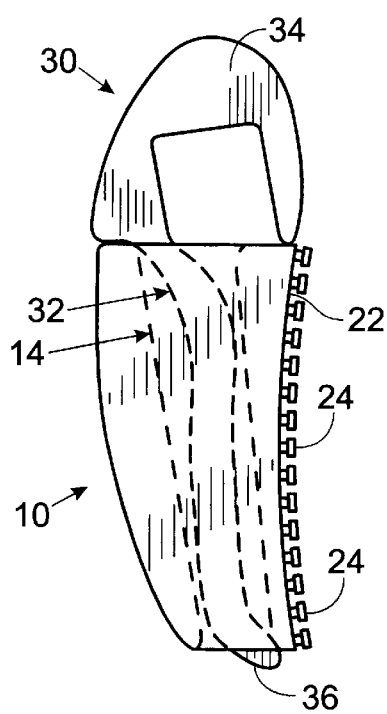
Fig. 4e
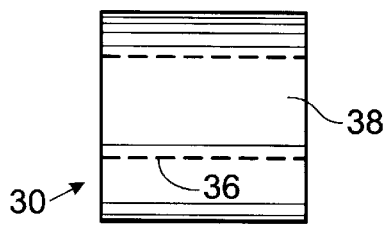

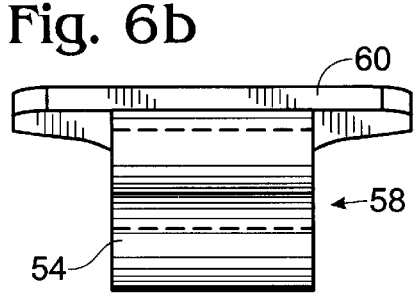
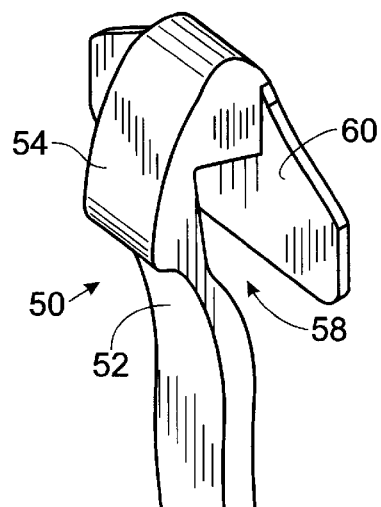
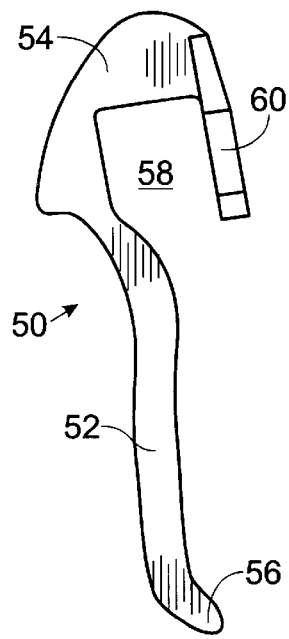
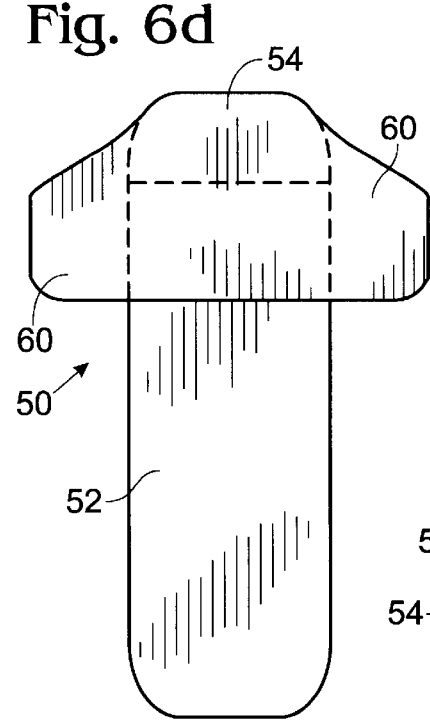
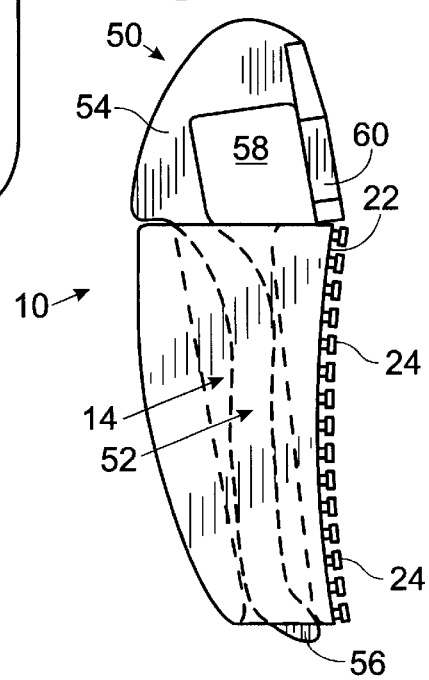
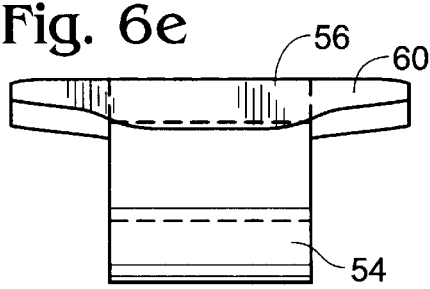

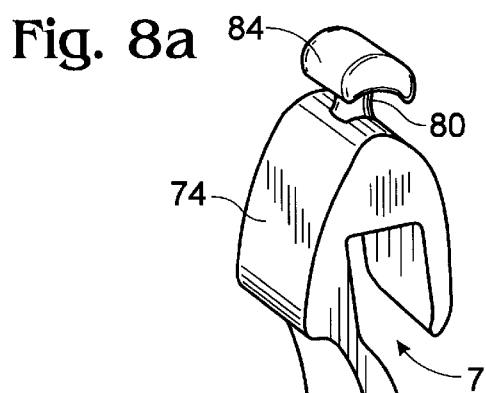
Fig. 8a
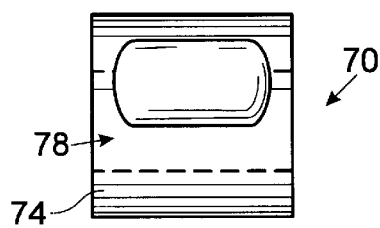
Fig. 8b
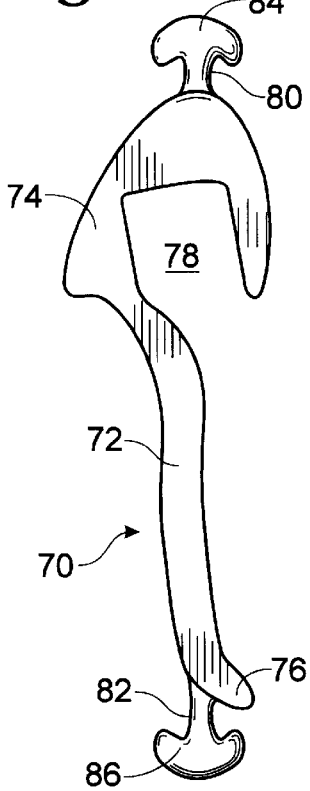
Fig. 8c
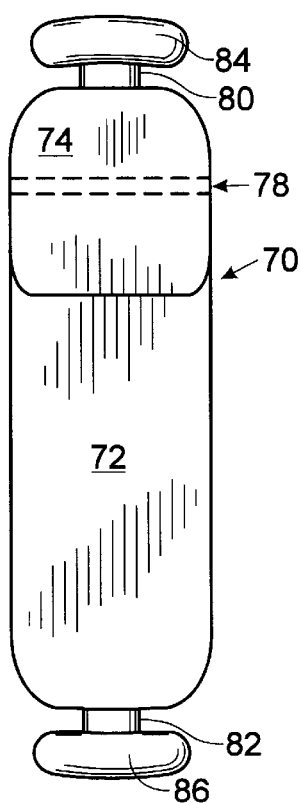
Fig. 8d
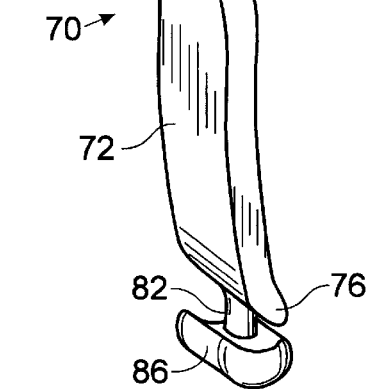
Fig. 8f
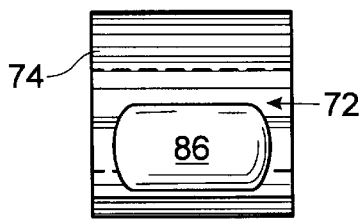
Fig. 8e
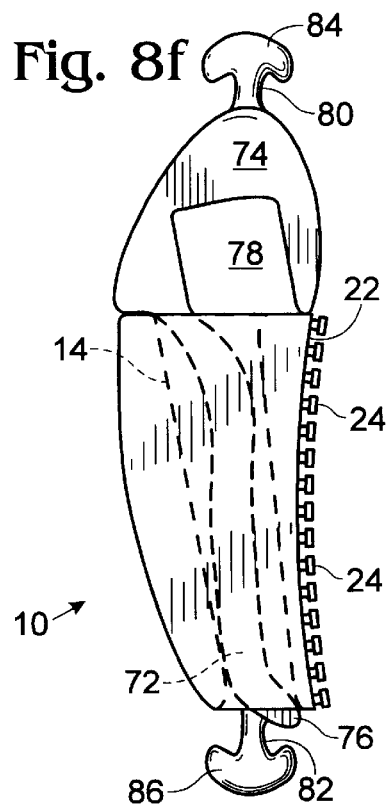

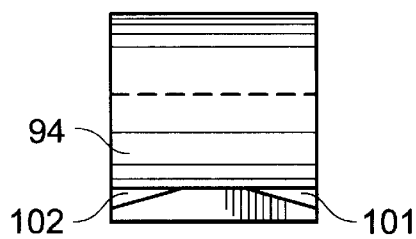
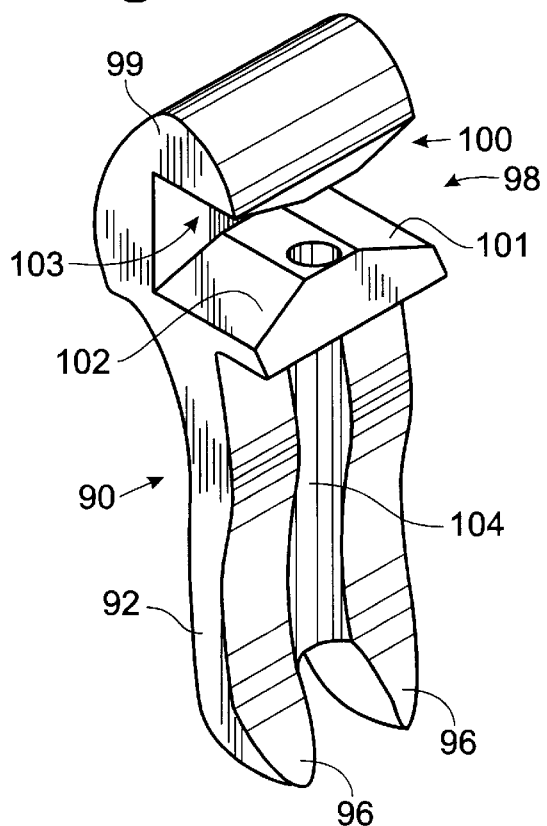
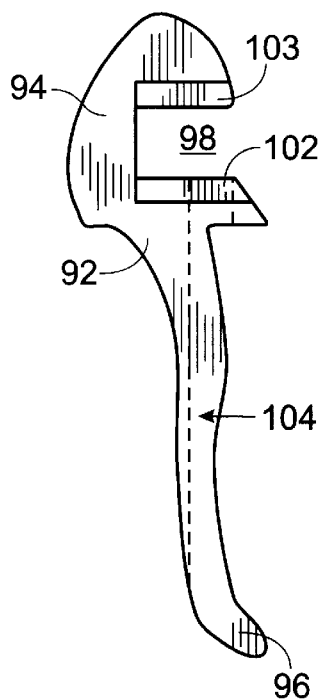
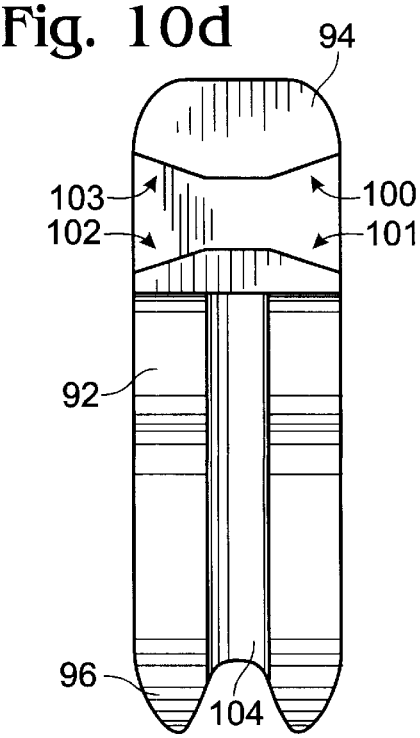
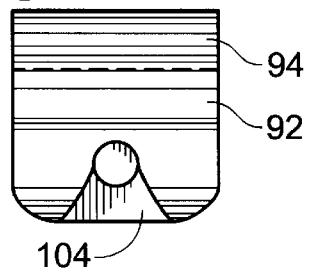

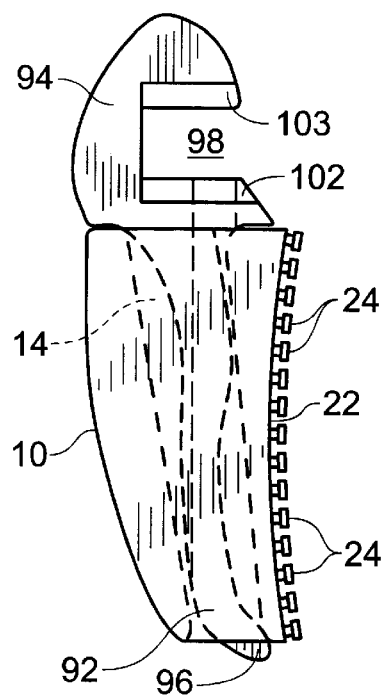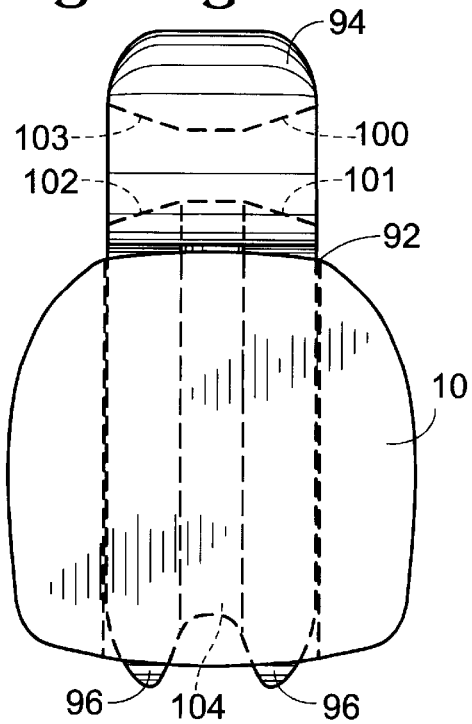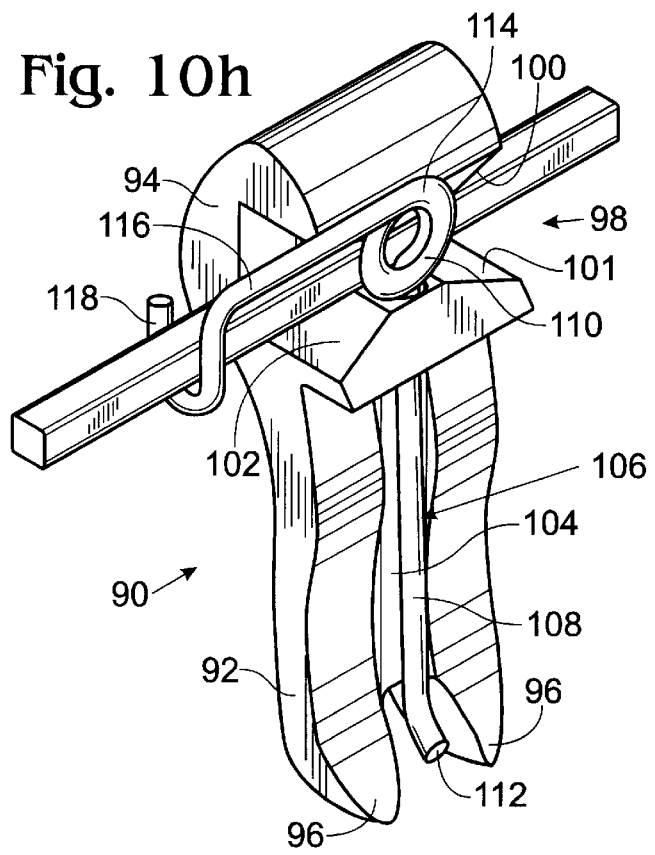

VERTICAL STRAIGHT WIRE ORTHODONTIC APLLIANCE HAVING INTERCHANGEABLE ANCHOR COMPONENTS

BACKGROUND OF THE INVENTION

1. Field of the Invention

The invention relates to the methods and apparatus of orthodontic practice, more specifically to the structure of appliances that when attached to the labial surfaces of teeth will apply thereto desired corrective forces so as to alter the physical disposition of those teeth, and in particular to appliances having a fixed base and replaceable anchor components that can be changed in accordance with the changing needs of an orthodontic patient without requiring removal of the bases from the teeth.

2. Background Invention

Orthodontics involves the application of corrective forces to teeth to change their physical disposition and orientation for purposes both of health and of aesthetic appearance. The parameters by which these features of a tooth are determined include the following:

Angulation: orientation of the central axis of a tooth in the mesial-distal direction relative to the vertical.

Torque: orientation of the central axis of a tooth in the lingual-labial direction relative to the vertical.

Rotation: an angle at which a transverse, symmetrically-bisecting plane through a tooth is oriented differently from a tangent plane through the arch taken at the position of the tooth.

Version: misplacement of the central axis of a tooth either away from or towards the midline of the arch, or along the curve of the arch.

Height: the vertical positioning of a tooth relative to the gum.

Particular types of tooth misplacement or orientation that are sought to be corrected by orthodontic procedures include the following, wherein "longitudinal" means along the direction of the arch, and "transverse" means at right angles thereto:

Mesial Angulation: the outer end of the tooth leans along the arch towards the front of the mouth.

Distal Angulation: the outer end of the tooth leans along the arch towards the back of the mouth.

Procline torque: the outer end of the tooth leans transversely to the arch in the labial direction.

Retrocline torque: the outer end of the tooth leans transversely to the arch in the lingual direction.

Labial version: transverse displacement of the central axis of a tooth in the labial direction.

Lingual version: transverse displacement of the central axis of a tooth in the lingual direction.

Mesial version: longitudinal displacement of the central axis of a tooth in the mesial direction.

Distal version: longitudinal displacement of the central axis of a tooth in the distal direction.

Intrusion: a lowered vertical height of a tooth relative to the plane of the arch.

Extrusion: an increased vertical height of a tooth relative to the plane of the arch.

These parameters may be altered by the use of a device that will apply one or more of:

Tipping: a rotational force applied to a tooth about an axis lying in the labial-lingual direction so as to change the angulation thereof.

Applied Torque: a rotational force applied to a tooth about an axis lying in the mesial-distal direction so as to correct the torque thereof.

Rotating: a rotational force about the central axis of the tooth.

Aligning force: a force applied transversely to the central axis of the tooth so as to correct version.

Distalize: applying a force transversely to the central axis of the tooth in the distal direction so as to correct mesial version.

Mesialize: applying a force transversely to the central axis of the tooth in the mesial direction so as to correct distal version.

Leveling: a force operating in the direction of the central axis of the tooth so as to correct intrusion or extrusion.

An early patent in the field is U.S. Pat. No. 2,378,279 issued Jun. 12, 1945 to Begg, in which a clamping device for acceptance of an arch is described that can be attached to a tooth by passing a band around the tooth and under a clamping screw. U.S. Pat. No. 4,674,978 issued Jun. 23, 1987 to Acevedo describes an appliance attached to the crown of the tooth so that the corrective forces exerted by arch wires connected therethrough are applied within a one-third distance from the gum line so as to bring about bodily movement of the tooth, the aforesaid appliance also being wedge shaped wherein the upper (when in a maxillary disposition) portion thereof is thicker than the lower portion, which itself gradually tapers nearly to a point towards the incisive edge of the tooth.

Consistent with much of the prior art in general, a characteristic of the device described in the Acevedo patent is that it has a fixed structure to which arch wires are fixedly attached by one means or another. In the course of the corrective process, whereby the disposition of selected teeth in terms of the parameters previously listed have been changed in some desired manner, should the orthodontic patient later require adjustment in the values of the corrective forces being applied, the particular brackets that have been used cannot be adjusted so as to provide the newly desired corrective forces. Other than by applying the common but uncertain process of bending arch wires so as to vary those forces, it will be necessary to remove those brackets and replace them with new brackets disposed in accordance with those newly acquired teeth parameters.

One attempt to provide some adjustment capability in orthodontic devices is shown in U.S. Pat. No. 3,423,833 issued Jan. 28, 1969 to Pearlman, which describes an orthodontic device having a base that attaches to a band encircling the tooth, together with a bracket that attaches to that base and that includes adjustment means whereby the slots of the bracket through which are passed one or more arch wires can be rotated in small increments so as to vary the nature of the tipping forces applied to the tooth. U.S. Pat. No. 3,521,355 issued Jul. 21, 1970 to Pearlman and U.S. Pat. No. 4,134,208 issued Jan. 16, 1979, also to Pearlman, describe adjustable positioning means by which orthodontic brackets can be accurately positioned vertically upon initial installation.

U.S. Pat. No. 4,797,095 issued Jan. 10, 1989 to Armstrong et al. describes an orthodontic bracket that is adapted for attachment directly to the tooth and that accommodates firstly an arch wire that is fixedly attached thereto and passes horizontally therethrough, and secondly a hook extending outwardly therefrom that may be connected at a distal end thereof through a rubber band or the like either to locations within the same arch so as to pull on the tooth as a displacement force, or to an opposite arch (i.e., from the maxillary arch to the mandibular arch or vice versa) so as to exert either a clockwise or a counter-clockwise rotational force thereon about a horizontal axis in the lingual-labial direction.

Similarly, a device that includes a lock spring pin adapted for tipping a tooth about a horizontal axis therethrough is described in U.S. Pat. No. 3,793,730 issued Feb. 26, 1974 to Begg et al. In this device, a modified form of the bracket type that is adapted for attachment to a tooth band includes an outwardly extending protrusion within which is included a vertical slot within which is inserted a spring pin having a U-shaped extension at the distal end thereof, and within that extension is mounted a spring and hook assembly adapted for hooking under an arch wire passing transversely therethrough so as to impart a tilting force on the tooth, either clockwise or counter-clockwise about a horizontal axis in the lingual-labial direction without needing to reach between arches. An earlier patent to Begg et al., U.S. Pat. No. 3,163,933 issued Jan. 5, 1965, employs a vertical pin within a bracket assembly to hold an arch wire within that bracket assembly.

A device adapted for turning a tooth about a vertical axis therethrough is described in U.S. Pat. No. 4,249,898 issued Feb. 10, 1981 to Andrews. An orthodontic bracket adapted to accept an arch wire is attached labially on a band encircling a tooth, and on a selected side of that bracket there is also attached an "S" or "U" shaped spring blade extending from the vicinity of the arch wire (i.e., at a predetermined distance from the band encircling the tooth) at its proximal end to the surface of the tooth band itself at its distal end, so as to exert an inward force that is displaced from the vertical axis of the tooth and thereby to exert a rotational torque thereon in the direction determined by the particular side of the bracket on which the spring blade was attached.

Another Andrews patent, U.S. Pat. No. 3,660,900 issued May 9, 1972, describes a bracket that attaches to a tooth band and includes a groove therein for purposes of receiving an arch wire, the horizontal angle of that groove being predetermined so as to provide a desired degree of tipping force to the tooth when a straight arch wire is passed therethrough. The device also incorporates a predetermined angle at which the bracket attaches to the tooth, so as to provide a desired degree of angulation force when the arch wire is passed therethrough, which effectively combines both tipping and torqueing corrections within a single bracket.

Such procedures, however, still do not allow the degree of readjustment in the forces applied to the tooth that may be required. The Pearlman devices do indeed provide limited means of adjusting those forces, i.e., rather than bending the arch wires, these have instead been placed within brackets that can themselves be rotated. However, such adjustments will have only limited effects as to the most desirable set of corrective forces to be applied in reference to the full range of orthodontic parameters previously listed. Other devices noted are of a single application type, meaning that with the exception of the Armstrong et al. '095 and the Andrews '900 patents, the devices serve only a single translational, rotational or other purpose, and must be unattached from the tooth (or tooth band) and then replaced by another device in the event that some different orthodontic procedure should be required. Moreover, much of the prior art as recited involves the use of tooth bands which are no longer thought to be required. It would be useful, therefore, to provide an orthodontic appliance that does not require the use of a tooth band in any event, but that also need not be removed and replaced at one or more intervals as the corrective process proceeds, and moreover an appliance within which changes in the specific applications thereof can easily be effected as to the full range of desired corrective forces, particularly as to the application of tipping and torqueing forces on a single tooth, and it is such an appliance that is provided by the present invention.

SUMMARY OF THE INVENTION

The invention comprises an orthodontic bracket having two main parts, i.e., (1) a base having a tapered, angled, and centrally disposed shaft passing longitudinally therethrough for acceptance therein of an arch wire anchor; and (2) for placement within that base, an arch wire anchor having (a) an undulated shank and (b) a head adapted to accept one or more arch wires passing therethrough, or alternatively one or more rubber bands or modules attached thereto. Different ones of said anchors, particular instances of each of which are further distinguishable in terms of torque angle, also incorporate heads of different design so as to provide means for imposing corrective forces relative to selected ones of the aforesaid parameters, thereby permitting adjustment to be made in the nature of the particular forces to be applied to each tooth as may be dictated in the course of the corrective orthodontic process. The ability to carry out such alternative procedures without requiring that the base be removed from the tooth surface is thus more efficient and cost effective, avoids repeated removal and replacement of devices on the enamel surface of the tooth as required in the devices of the prior art, and thereby avoids compromising the integrity of the tooth surface each time that a device is removed.

BRIEF DESCRIPTION OF THE DRAWINGS

Preferred embodiments of the invention are illustrated in the following figures, in which like elements are indicated by like numerals:

FIGS. 4a–4f show different views of a first embodiment of the anchor portion of the invention, both separately and as installed within the base of FIGS. 3a–3f.

FIGS. 6a–6f show different views of a second embodiment of the invention, both separately and as installed within the base of FIGS. 3a–3f.

FIGS. 8a–8f show different views of a third embodiment of the invention, both separately and as installed in the base of FIGS. 3a–3f.

FIGS. 10a–10g show different views of a fourth embodiment of the invention, both separately and as installed in the base of FIGS. 3a–3f.

FIGS. 10h–10n show different views of the fourth embodiment of the invention as shown in FIGS. 10a–10g with the addition of a tipping wire.

DETAILED DESCRIPTION OF THE INVENTION

Figure 1:
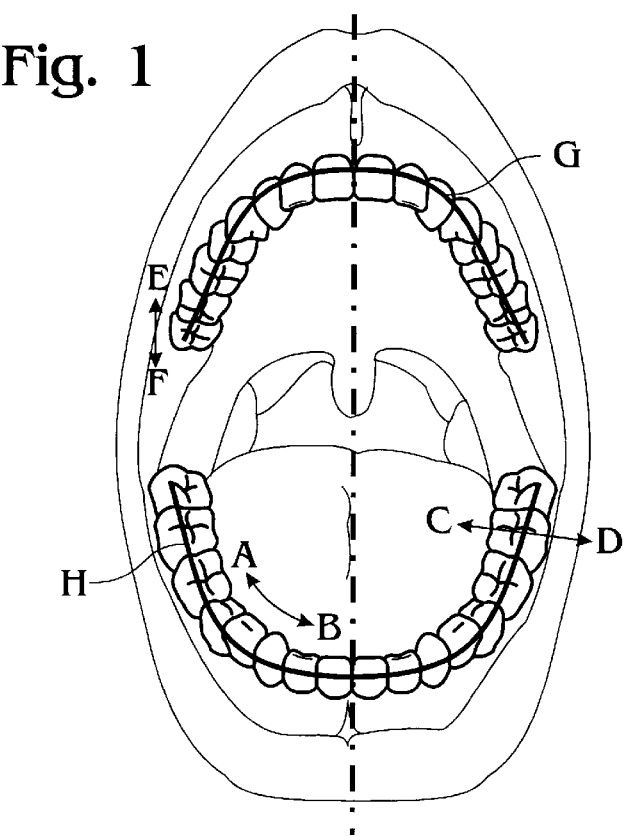
FIG. 1 shows views of the maxillary and mandibular arches and defines the directions thereon as are employed in the text.

FIG. 1 from the prior art shows the maxillary and mandibular arches, onto which are placed letter codes and arrows that define the directions specified in the following Table I:

TABLE I

| | | | |
|---|---|---|---|
| A = | Distal | D = | Labial |
| B = | Mesial | E = | Gingival |
| C = | Lingual | F = | Occlusal |

The letter G in FIG. 1 designates the maxillary arch and the letter H designates the mandibular arch, one or the other of which are used in FIG. 1 to define the directions of Table I, but it should be understood that a direction as defined with respect to one arch applies equally as will in reference to the other arch.

To facilitate depiction of various aspects of the invention, the types of tooth displacement that are ordinarily corrected by orthodontic procedures are illustrated in FIGS. 2a–2j, and the nature of the displacement corresponding to each illustration is noted in the following Table II:

TABLE II

| | | | |
|---|---|---|---|
| 2a | Mesial Angulation | 2f | Lingual Version |
| 2b | Distal Angulation | 2g | Mesial Version |
| 2c | Procline Torque | 2h | Distal Version |
| 2d | Retrocline Torque | 2i | Intrusion |
| 2e | Labial Version | 2j | Extrusion |

As described in the prior art, orthodontic brackets have been of various types, but of a common form wherein the bracket is attached to the tooth and accommodation is made in one way or the other for attachment of wires that serve to apply desired forces to the tooth. In practice, the type of force required for correction of the positioning of a tooth is determined, and then the particular type of bracket that will provide such a force is glued to the tooth and the necessary wires, rubber bands or the like are connected therethrough. By contrast, the present invention comprises an orthodontic bracket consisting of a base into which is to be inserted an anchor having a head portion, and wires or the like are attached to or threaded through that anchor head. A change in the types of force required on a tooth, as a result of the cumulative effect of an applied force overtime, does not in the apparatus comprising the invention require removal of an installed bracket from the tooth and replacement with a new bracket, but only a replacement of the anchor within the installed base. The general structure of the base element of the invention is shown in FIGS. 3a–3e.

Figure 3A:
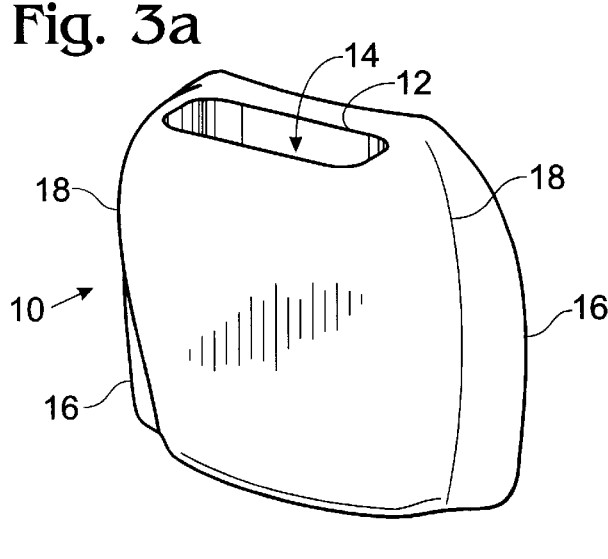
FIGS. 3a–3f show different views of a preferred embodiment of the base portion of the invention.
Figure 3F:
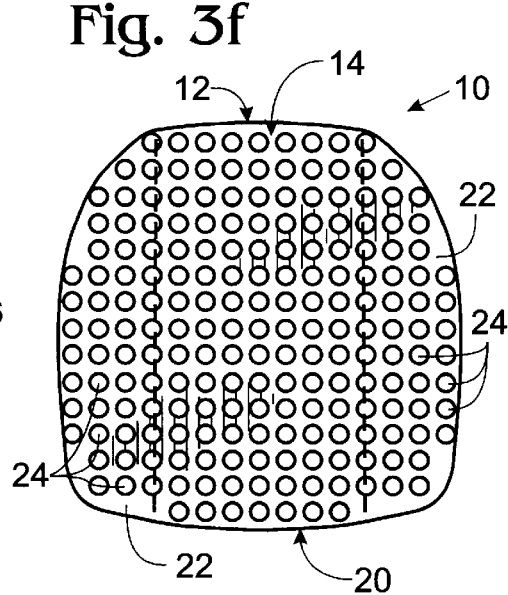
Figure 3B:
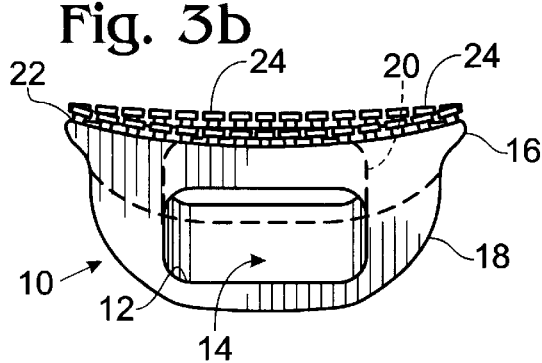
Figure 3C:
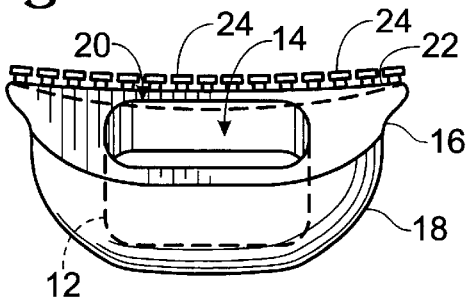

Specifically, FIG. 3a is a perspective view of a base 10 within which may be seen an upper end 12 of anchor aperture 14 descending vertically therethrough. In general structure, and as also seen in FIGS. 3b–3c, base 10 is formed along a first arc 16 to a first depth encompassing the full width of base 10, onto which is superimposed a narrower second arc 18 of a second depth. Anchor aperture 14 encompasses the parts of base 10 defined both by first arc 16 and second arc 18.

FIG. 3b is a top plan view of base 10 of FIG. 3a, again showing upper end 12 of anchor aperture 14. Lower end 20 of anchor aperture 14 is shown in outline in FIG. 3b. Also shown in FIG. 3b is a curved inner surface 22 (facing onto the tooth surface to which base 10 will be attached) along which are disposed an array of contact points 24 (for clarity in this drawing, only two horizontal rows of such contact points 24 are shown).

Figure 3D:
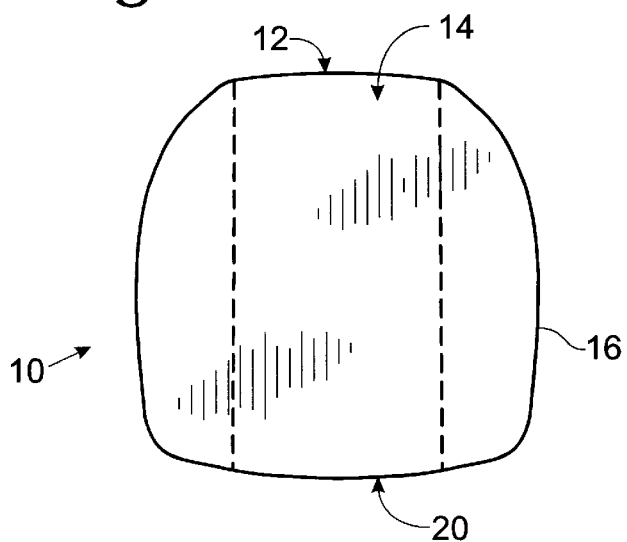
Figure 3E:
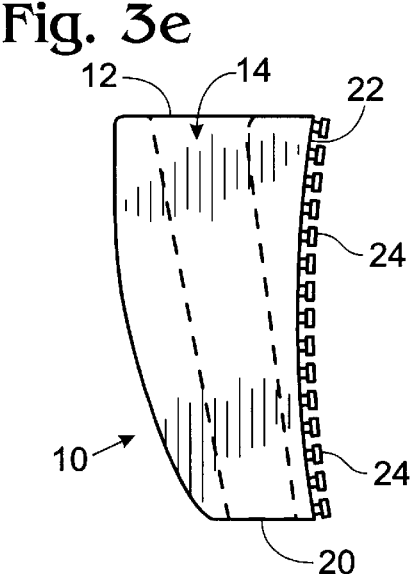

FIG. 3c is a bottom plan view of base 10, in which lower end 20 of anchor aperture 14 is now shown in a solid line, upper end 12 of anchor aperture 14 is shown in outline, and other visible elements are indicated by numbers corresponding to those of FIG. 3b. FIG. 3d is a front elevation view of base 10, in which the two vertical dashed lines show the lateral extent of anchor aperture 14 that lies therewithin, in which like elements are again indicated by like numbers. FIG. 3e is a side elevation view of base 10 showing inner surface 22, in this case a single column of contact points 24, and two slanted, dashed lines which depict the front-to-back extent of anchor aperture 14, other like elements again being indicated by like numbers. Finally, FIG. 3f is a rear elevation view of base 10 in which contact points 24 are seen to be lain out on inner surface 22 in a rectangular array, with other like elements again being indicated by like numbers.

In use, base 10 is glued onto the front surface of a tooth in accordance with the normal practice of orthodontics with regard to prior art brackets. Replicates of base 10 are installed on the labial surfaces of the teeth to be treated, and either before or after such installation, particular anchor types selected for particular orthodontic purposes are placed within base 10. A first such anchor type is shown in FIGS. 4a–4f.

Specifically, FIG. 4a is a perspective view of a first anchor 30, which is seen to comprise an elongate, undulated first shank 32 having at one end thereof a first head 34, and at the opposite end thereof a first lip 36 that serves to oppose withdrawal of first anchor 30 once the same has been installed within a base 10. A wire slot 38 passes transversely through first head 34.

FIG. 4b is a top plan view of first anchor 30 of FIG. 4a, and FIGS. 4c–4e are respectively a side elevation view, a front elevation view, and a bottom plan view thereof, like elements having like numerals associated therewith in each case. FIG. 4f is a side elevation view of first anchor 30 as installed within base 10 of FIGS. 3a–3e, showing in particular the disposition of shank 32 (indicated by the two inward-most dashed lines) of first anchor 30 within anchor aperture 14 (indicated by the two outward-most dashed lines) of base 10. For purposes of clarity in the drawing, the two pairs of dashed lines that respectively define first anchor shank 32 and anchor aperture 14 are shown not to be in contact, but it will be understood that the specific purpose in providing anchor shank 32 with the indicated undulatory structure is to permit a force fit of first anchor shank 32 within anchor aperture 14, said fit then being held in place in part by first lip 36.

Figure 5A:
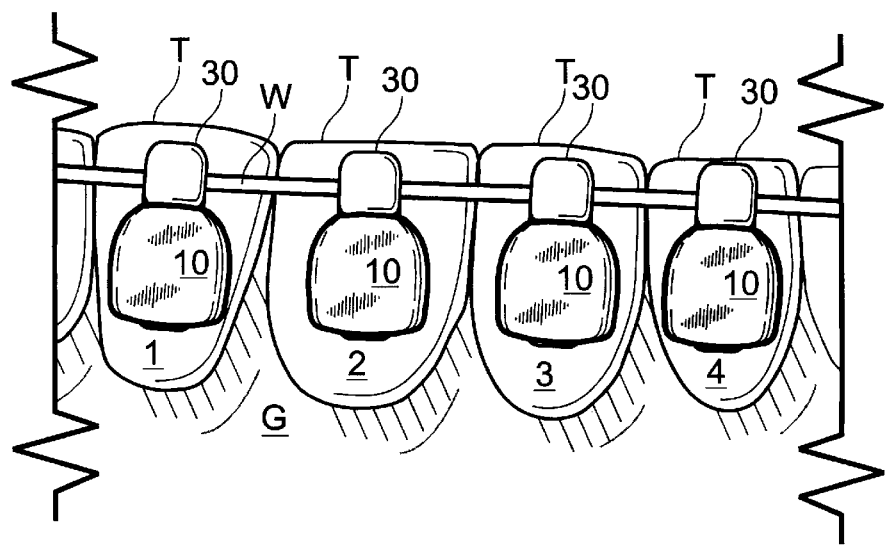
FIGS. 5a–5c illustrate a use of the anchor and base of FIGS. 4a–4f to the process of leveling a tooth.
Figure 5B:
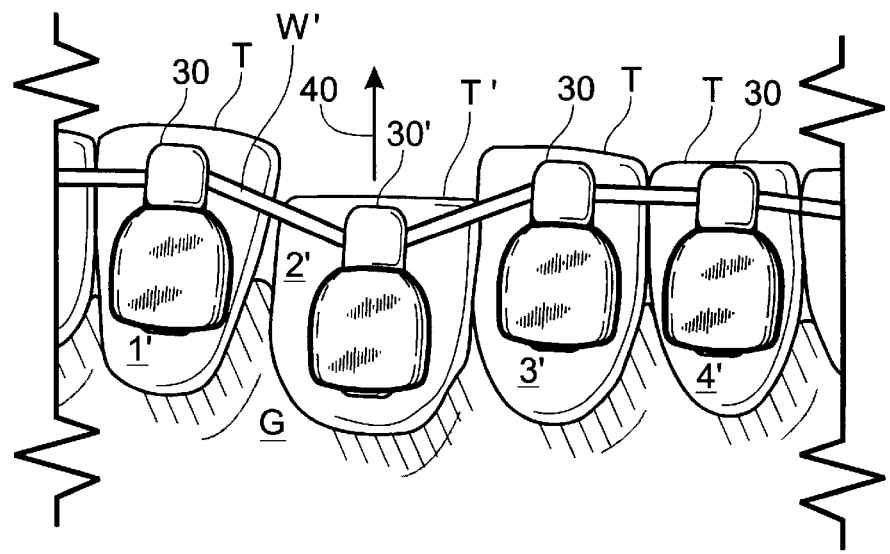
Figure 5C:
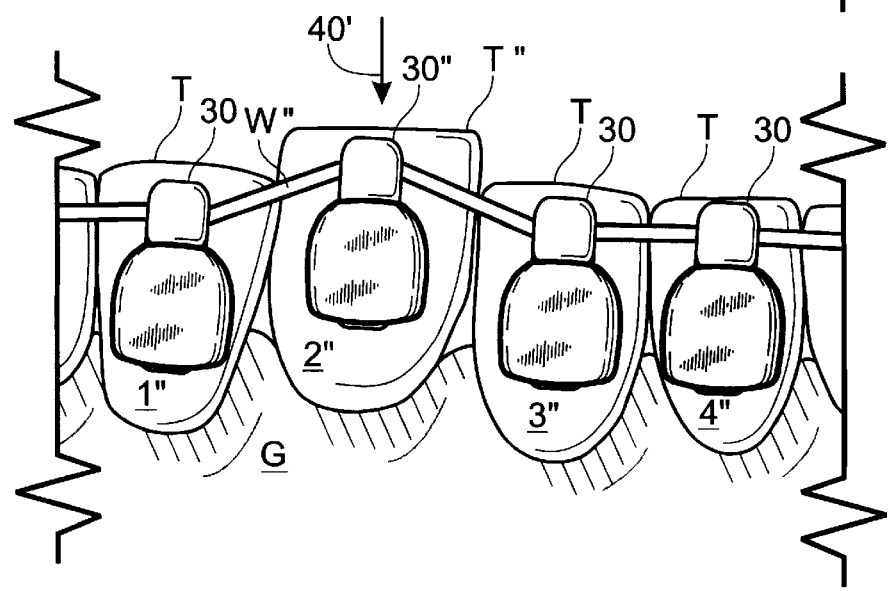

FIGS. 5a–5c illustrate an application of base 10 and first anchor 30 in an orthodontic leveling process, wherein a tooth happens to be positioned either higher (extrusion) or lower (intrusion) than is normal relative to its neighbors, and orthodontal processes are utilized to correct that condition.

As a first part of that illustration, FIG. 5a shows a front elevation view of four neighboring teeth 1–4 within the mandibular arch for which no orthodontic correction is required, e.g., these teeth represent a case in which the tops T of the teeth extend to normal heights above gum G, so that base 10 and first anchor 30 may serve merely to support an arch wire W that is being extended to some other part of the mouth for some other corrective purpose. (The actual size and placement of wire W as shown in FIG. 5a, or of other wires shown elsewhere herein, are used for illustrative purposes only, the actual sizes and placement of such wires as used in orthodontic practice being well known to those of ordinary skill in the art.)

Figure 5D:
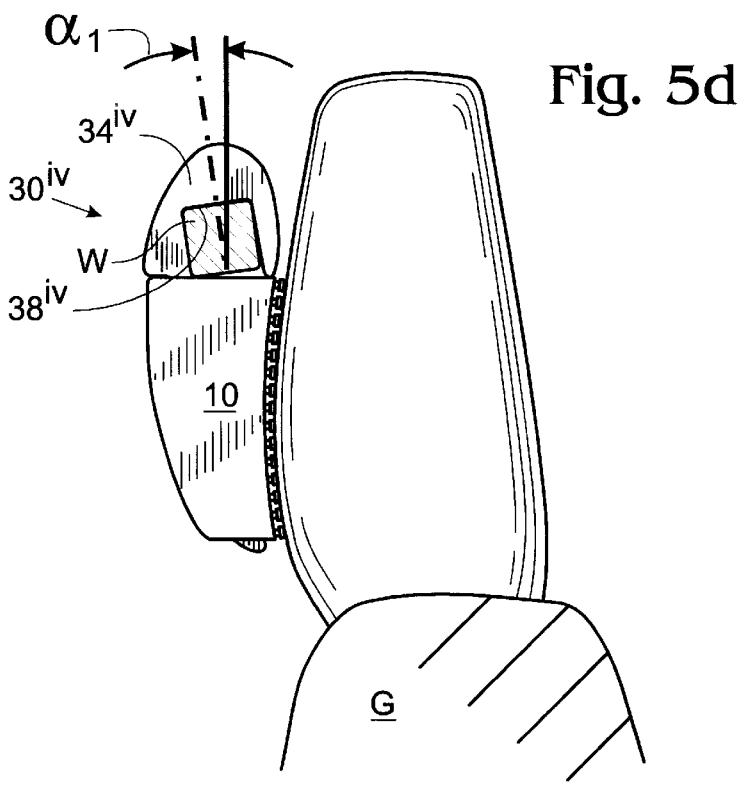
FIGS. 5d–5g illustrate a use of the anchor and base of FIGS. 4a–4f, and of variations thereof, to the process of applying a corrective torque to a tooth.

By contrast, FIG. 5b shows in quite exaggerated form four adjacent teeth 1'–4' in which tooth 2' is intruded (e.g., as shown earlier in FIG. 2l as to the maxillary arch), wherein top T' thereof terminates below the level of its neighbors, and for that purpose a first anchor 30' that is in a lower position than adjacent first anchors 30 is utilized to create, by a downward bending of wire W', an upward (occlusal) force on that tooth as shown by arrow 40. Similarly, FIG. 5c shows, also in exaggerated form, four adjacent teeth 1"–4" in which 2" tooth is extruded (e.g., as shown earlier in FIG. 2j as to the maxillary arch) wherein top T" thereof extends above the level of its neighbors, and for that purpose a first anchor 30" that is positioned higher than adjacent first anchors 30 is utilized to create, by an upward bending of wire W", a downward force on that tooth as shown by arrow 40'. (As can be seen in FIG. 5d below, a downward force on wire W", or indeed on any wire disposed within one of the anchors comprising the invention, actually places the same against the top of base 10.) The foregoing discussion is made in reference to the upwardly-pointing teeth of the mandibular arch, but of course corresponding principles and usages will apply to the downwardly pointing teeth of the maxillary arch as well.

Another feature of first anchor 30 should relates to the degree of undulation provided to first anchor shank 32. As is known to ordinary practitioners in the art, for proper orthodontic purposes there exists an upper limit to the degree of force that ought to be applied to a tooth so as to avoid doing damage thereto. That limit can be implemented "automatically" within the design of first anchor 30 by pre-determination, in accordance with standard mechanical engineering principles, of the amount of undulation therein and the tensile strength thereof. Specifically, a first anchor 30 that is used to apply an occlusal pulling force on a tooth is constructed so that when an application of a force beyond that limit is attempted, that force will not operate on the tooth but will instead pull first anchor 30 out of base 10. The orthodontic practitioner is then made aware that an excess force was sought to be applied, and will instead raise the placement of base 10 on the tooth so that the upward force to be exerted thereon will be lessened.

Yet another application of variations of first anchor 30 is shown in FIGS. 5d–5g. In the case of procline or retrocline torque in the tooth, as shown respectively in FIGS. 2c and 2d, a corrective torque can be applied so as to counter the existing torque and thereby improve the positioning of the tooth. For this particular purpose, it is significant that the arch wires shown in FIGS. 5d–5g are of rectangular rather than circular cross-section, so that any twist imparted to such a wire will result in a torsional restoring force from the wire. Of course, any other arch wires that may be shown herein as having a rectangular cross-section may, and in practice often do, have a round cross-section. Such arch wires are shown as being rectangular in cross-section herein, however, to suggest again that various ones of the anchors that comprise the invention may be used in combination, and if any such combination of desired orthodontic procedures happens to include a torque correction as is now to be described, then the use of a wire having a rectangular cross-section is necessary and can indeed be used in conjunction with arch types and procedures not involving torque corrections.

Figure 5E:
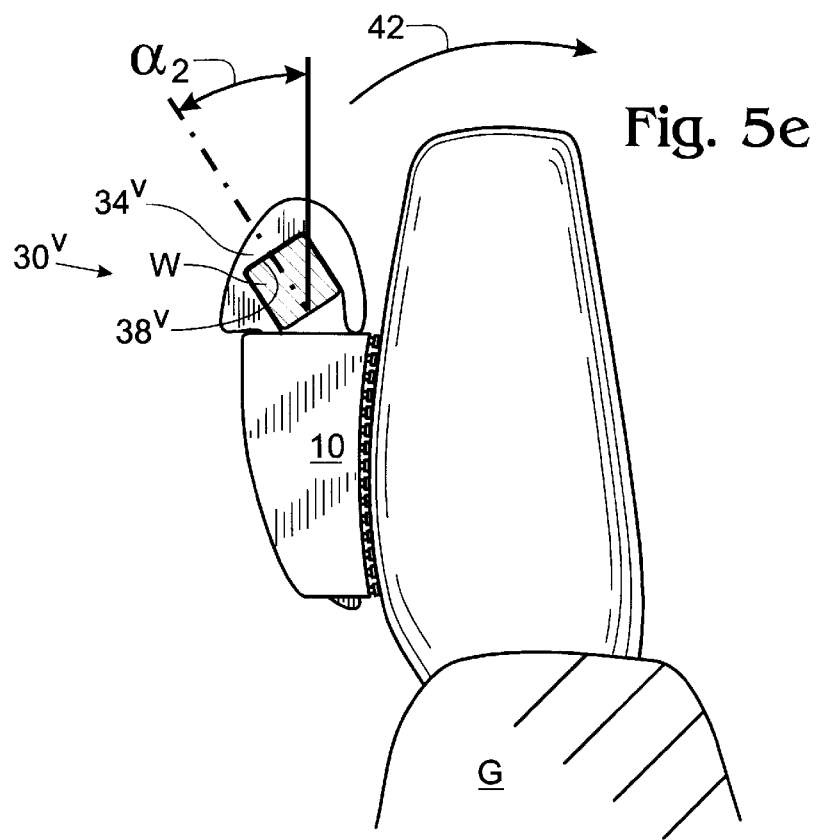
Figure 5F:
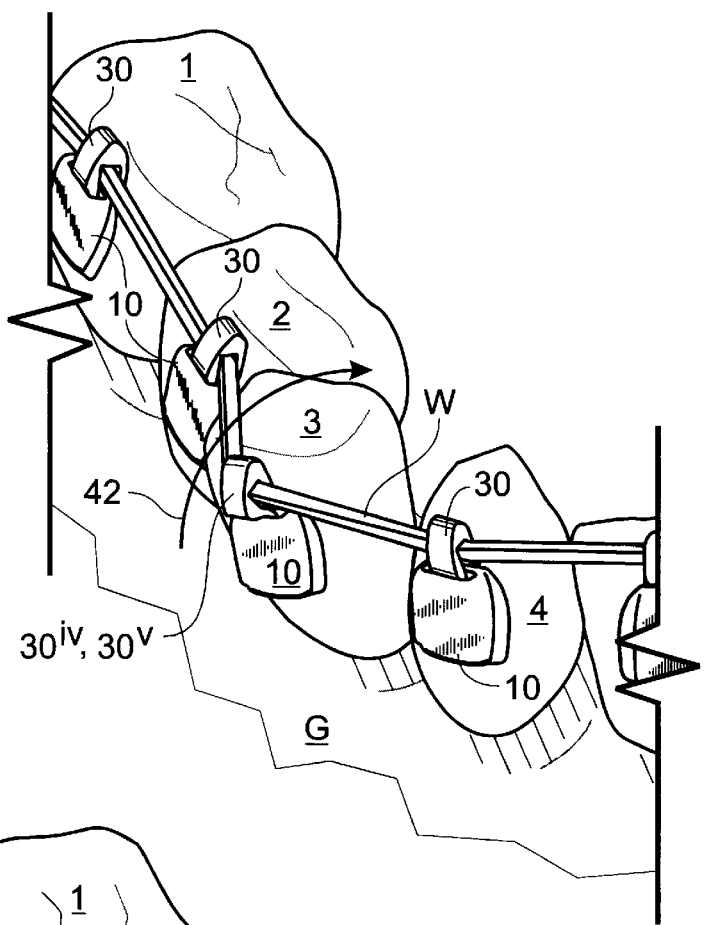
Figure 5G:
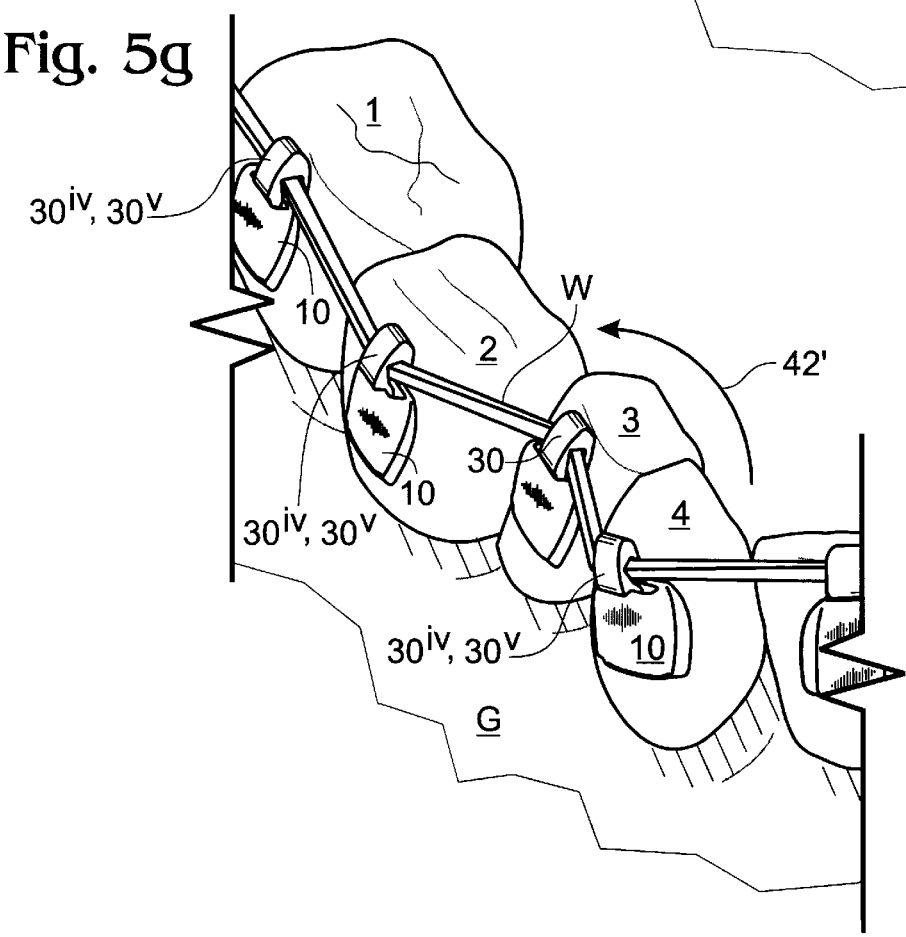

FIGS. 5d–5e show side elevation views of modified first anchors $30^{iv}$ and $30^v$ in which the central planes of the respective wire slots $38^{iv}$, $38^v$ have been given different angles $\alpha_1$ and $\alpha_2$ (wherein $\alpha_2 > \alpha_1$) away from the tooth. As now shown exaggerated form in FIG. 5f, if either of first anchors $30^{iv}$ or $30^v$ is used on a tooth (e.g., tooth 3) having adjacent teeth (2 and 4) on which were installed first anchor 30 of FIG. 4f (in which first wire slot 38 of first head 34 is assumed to be oriented to the tooth at an angle smaller than either of $\alpha^1$ or $\alpha^2$), a wire W of rectangular cross section passing between such adjacent teeth through wire slot $38^{iv}$ or $38^v$, that are likewise rectangular in cross-section, will exert an inwardly directed torque as shown by curved arrow 42 so as to counteract any procline torque of the tooth. Conversely, as shown in similarly exaggerated form in FIG. 5g, if either of modified first anchors $30^{iv}$ or $30^v$ is now used as the norm in passing around the arch, but first anchor 30 of FIG. 4f is applied to an intervening tooth (e.g., tooth 3), an outward torque as shown by curved arrow 42' will be exerted on that tooth so as to correct the retrocline torque of the tooth.

FIGS. 6a–6f show a second anchor type 50. Specifically, FIG. 6a is a perspective view of second anchor 50 that, similarly to first anchor 30, has an elongate, undulating second shank 52, a second head 54 at one end thereof, and at the opposite end thereof a second lip 56. A second wire slot 58 passes transversely through second head 54. Second anchor 50 differs from first anchor 30 principally in that second head 54 thereof includes a lateral extension 60 that extends bilaterally therefrom (as in the top of a "T") on the side thereof that when second anchor 50 is installed within base 10 will face towards the tooth. As will be shown below, extension 60 provides a force that will tend to rotate a tooth.

FIG. 6b is a top plan view of second anchor 50 of FIG. 6a, and FIGS. 6c–6e are respectively a side elevation view, a front elevation view, and a bottom plan view thereof, like elements having like numerals associated therewith in each case. FIG. 6f is a side elevation view of second anchor 50 as installed within base 10 of FIGS. 3a–3e, showing in particular the disposition of shank 52 (indicated by the innermost pair of dashed lines) of second anchor 50 within anchor aperture 14 (indicated by outermost pair of dashed lines) of base 10. It should be understood that as in the case of first anchor 30, the particular torque angle of second anchor 50 as shown is arbitrarily selected, and may be varied for purposes of specific orthodontic applications. In particular, the type of variation in angulation described above with reference to first anchor 30 (i.e., to correct procline torque or retrocline torque) can be employed in conjunction with the rotational correction now to be described.

Figure 7A:
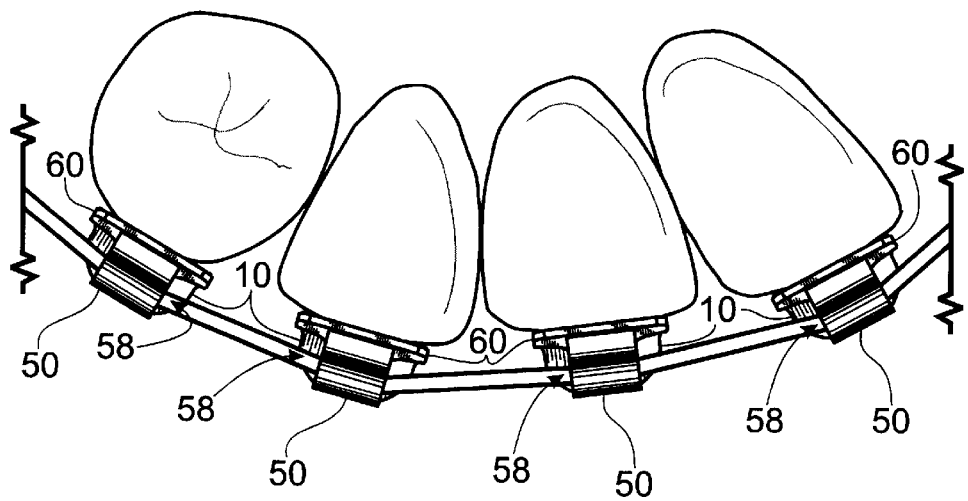
FIGS. 7a–7c illustrate a use of the anchor and base of FIGS. 6a–6f to the process of rotating a tooth.
Figure 7B:
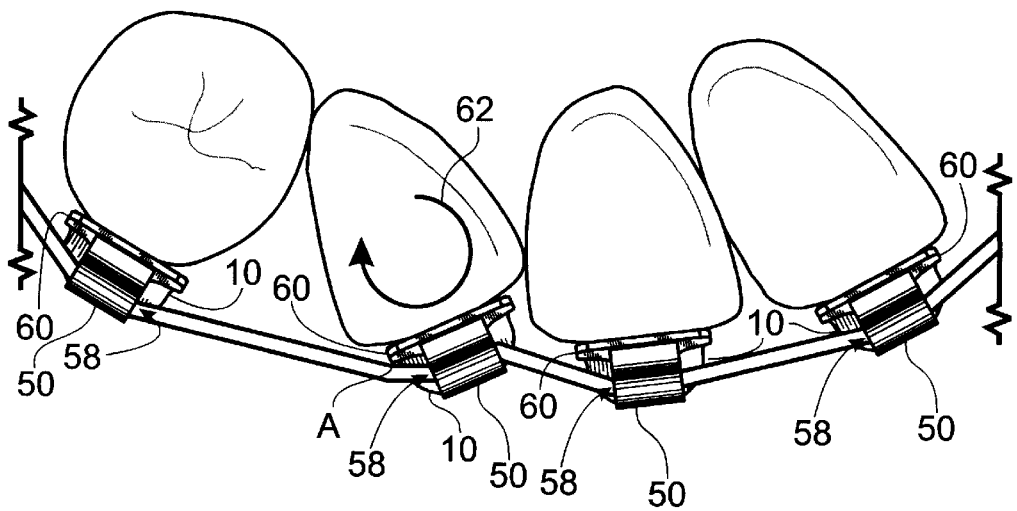
Figure 7C:
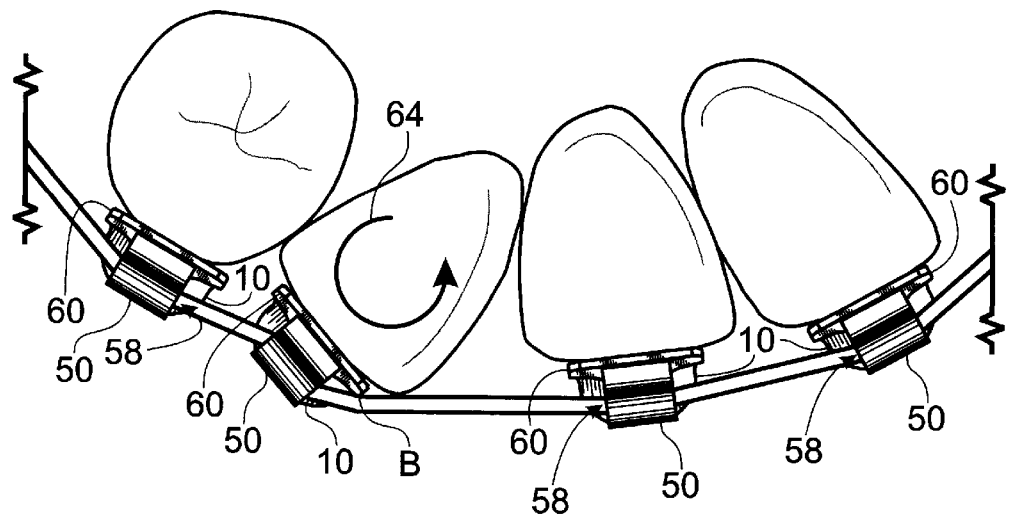

An application of second anchor 50 is shown in FIGS. 7a–7c, wherein FIG. 7a is a top plan view of an array of four teeth in an ordinary arch, and with second anchors 50 installed within bases 10 attached to those teeth, together with a wire passing through wire slot 58. With respect to teeth that are properly positioned in terms of rotation about their long axes, the presence of lateral extension 60 has no effect on the tooth.

In FIG. 7b, however, a tooth is shown that is rotated relative to the teeth on either side thereof, i.e., the second tooth in passing from left to right is rotated counterclockwise with respect to the first and third teeth. Upon installing a base 10 and second anchor 50 onto the front plane of that second tooth, the indicated base 10 and second anchor 50 are likewise rotated relative to those elements as installed on the neighboring teeth, such that the leftward side of lateral extension 60 comes into contact with the wire at point A so as to create an additional and asymmetrical force. The resultant of that force acting on that second tooth is shown as circular arrow 62, i.e., a clockwise rotational force that will tend to correct the counter-clockwise rotational misplacement of the tooth. In FIG. 7c, the same effect is shown with respect to a second tooth that is rotationally displaced in a clockwise direction, i.e., upon placement of base 10 and second anchor 50 as before, the right-ward side of lateral extension 60 comes into contact with the wire at point B so as to result in the counter-clockwise rotational force on that second tooth shown as circular arrow 64.

FIGS. 8a–8f show a third anchor type 70. Specifically, FIG. 8a is a perspective view of third anchor 70 that, similarly to first anchor 30 and second anchor 50, has an elongate, undulating third shank 72, a third head 74 at one end thereof, and at the opposite end thereof a third lip 76. A third wire slot 78 passes transversely through third head 74. Third anchor 70 differs from first anchor 30 and second anchor 50 principally in that third head 74 thereof includes first and second anchor posts 80, 82 disposed centrally to the axis of third shank 72 at opposite ends thereof, i.e., respectively atop third head 74 and beneath third lip 76. First and second anchor posts 80, 82 further comprise respectively first and second plates 84, 86 centrally disposed at respective distal ends thereof.

FIG. 8b is a top plan view of third anchor 70 of FIG. 8a, and FIGS. 8c–8e are respectively a side elevation view, a front elevation view, and a bottom plan view thereof, like elements having like numerals associated therewith in each case. FIG. 8f is a side elevation view of third anchor 70 as installed within base 10 of FIGS. 3a–3e, showing in particular the disposition of shank 72 (indicated by the innermost pair of dashed lines) of third anchor 70 within anchor aperture 14 (indicated by the outermost pair of dashed lines) of base 10. It should be understood that as in the case of first anchor 30 and second anchor 50, the particular torque angle of third anchor 70 as shown is arbitrarily selected, and may be varied for purposes of specific orthodontic applications when employed with (i.e., adjacent to) anchors of the same or other types that likewise have selected torque angles.

Figure 2A:
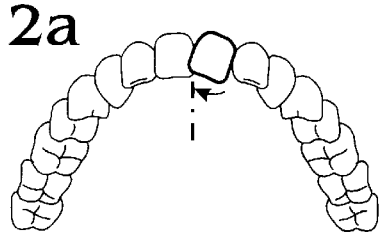
FIGS. 2a–2j show the types of tooth displacement that are typically correctable by orthodontic procedures.
Figure 2B:
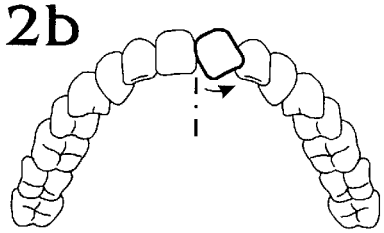
Figure 2C:
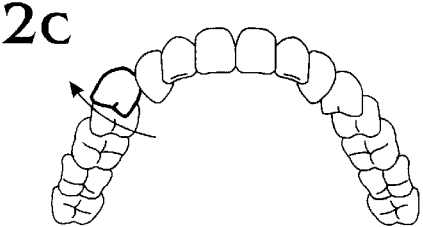
Figure 2D:
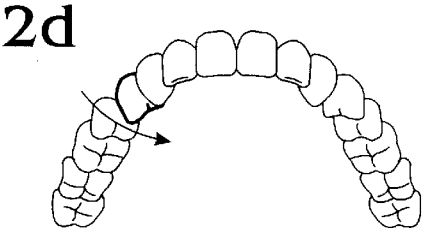
Figure 2E:
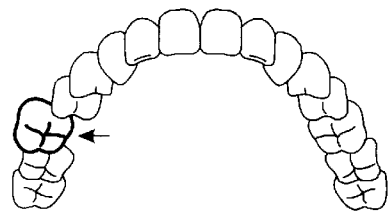
Figure 2F:
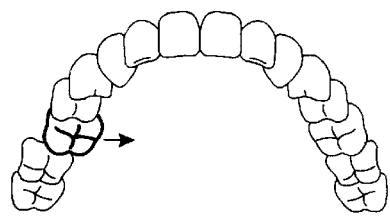
Figure 2G:
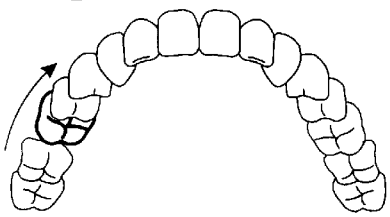
Figure 2H:
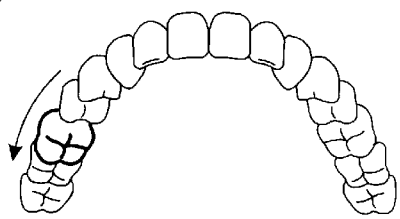
Figure 2I:
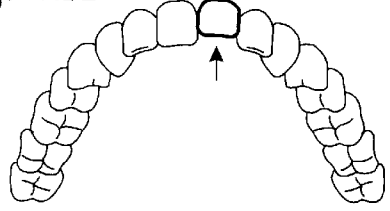
Figure 2J:
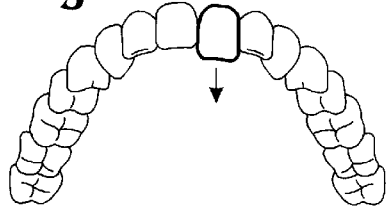
Figure 9:
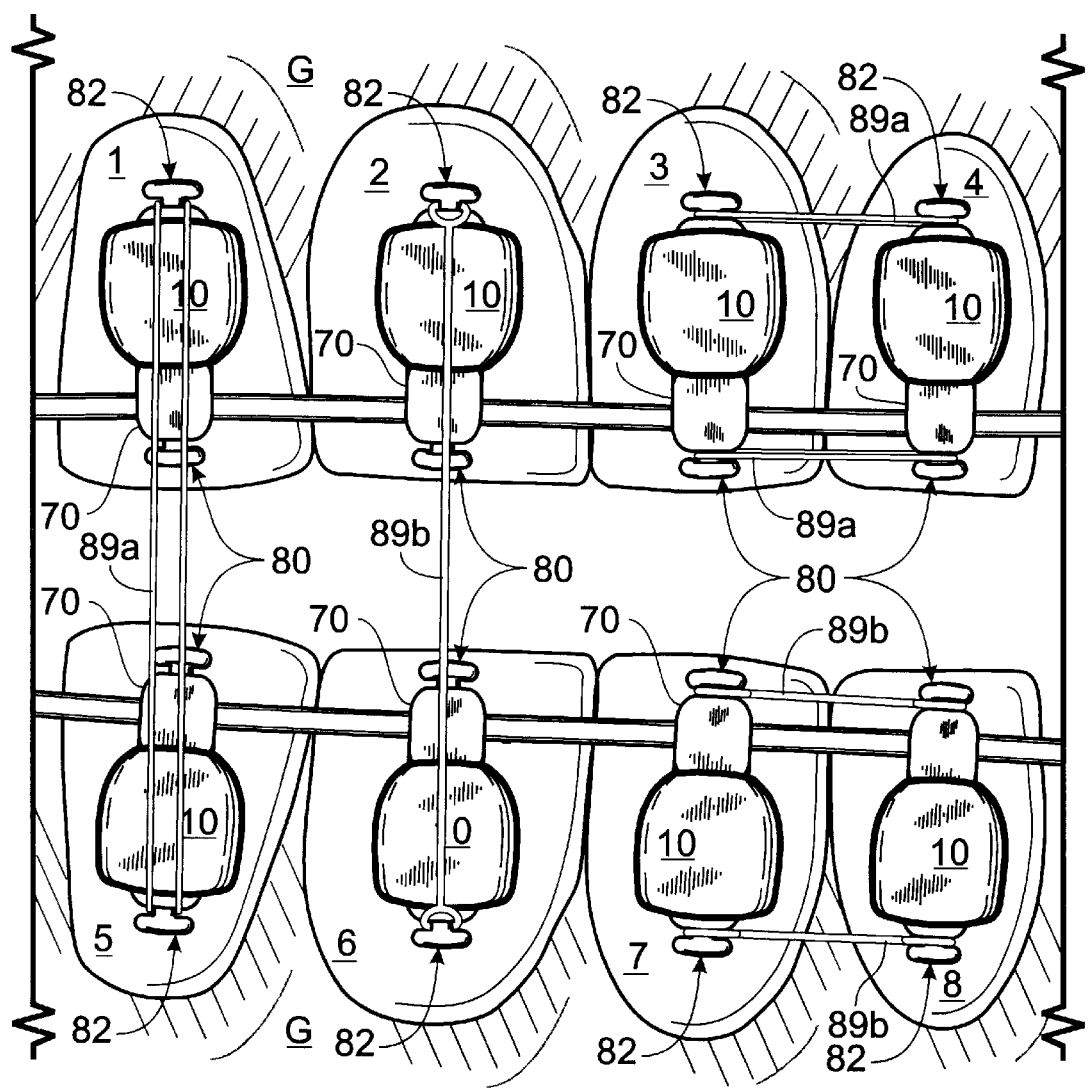
FIG. 9 illustrates uses of the anchor and base of FIGS. 8a–8f to the process of correcting intrusion or extrusion, or of displacing a tooth laterally.

For purposes of illustrating the application of third anchor 70 to cases of intrusion or version, FIG. 9 shows in a front elevation view an assemblage of eight teeth, four in the mandibular arch and four in the maxillary arch, on which each of which are installed instances of base 10 and third anchor 70. The method of correcting intrusion (as shown in FIG. 21) is shown as to teeth 1–2 and 5–6, and of correcting mesial or distal version (as shown in FIGS. 2g and 2h) is shown as to teeth 3–4 and 7–8. On the left side of FIG. 9a rubber band 89a is shown to have been stretched from a post 82 of a third anchor 70 installed on tooth 1 to a corresponding post 82 of a third anchor 70 installed on tooth 5. A similar process is shown as between teeth 2 and 6, except that a module 89b is used, a "module" simply being an elongate elastic band that has apertures on opposite ends thereof for engaging a structure such as post 82. If either of rubber band 89a or module 89b is extended in a stretched configuration between teeth of opposing arches as indicated, an occlusal force will be exerted on both teeth so connected so as to tend to correct any intrusion of one or the other.

For the correction of medial or distal version, third anchors 70 may be placed within bases 10 that are attached to a tooth exhibiting such displacement, and also to another tooth in the direction (distal or mesial) in which movement of the tooth is desired so as to correct such (mesial or distal, respectively) version. Thus, a rubber band 89a is shown on the right hand side of FIG. 9 to have been stretched laterally between posts 82 of third anchors 70 installed on teeth 3 and 4, and a second rubber band 89a between posts 80 on opposite ends of those same third anchors 70. Similarly, a module 89b is shown to have been stretched between posts 82 of third anchors 70 installed on teeth 7 and 8, and a second module 89a between posts 80 on opposite ends of those same third anchors 70. Either one of those third anchors 70 that are installed on teeth 3 and 4, and likewise as to those installed on teeth 7 and 8, may be further connected in a rigid manner to additional teeth extending laterally therefrom, so that the elastic force exhibited by rubber bands 89a or modules 89b will extend from such an array of rigid teeth on one side to the tooth requiring correction on the other side, so that it is the tooth requiring correction that must move in order to lessen that elastic force.

FIGS. 10a–10h show yet another embodiment of the invention, specifically in fourth anchor 90 that accommodates tipping of a tooth about a horizontal axis lying in the lingual-labial direction. FIG. 10a is a perspective view of fourth anchor 90 that, similarly to the previous three embodiments, includes an elongate, undulating fourth shank 92, a fourth head 94 at one end thereof, and at the opposite end thereof a fourth lip 96. A fourth wire slot 98 passes transversely through fourth head 94. Fourth anchor 90 differs from the previous embodiments principally in that fourth wire slot 98 includes first—fourth notches 100–103 at the four corners thereof, i.e., so as to yield in cross-section a "butterfly" shape as best seen in FIG. 10d; and secondly in having spring slot 104 extending longitudinally through that face of fourth anchor 90 that faces towards the tooth when fourth anchor 90 is placed within anchor aperture 14 of base 10 in the manner previously described.

FIG. 10b is a top plan view of fourth anchor 90 of FIG. 10a, and FIGS. 10c–10e are respectively a side elevation view, a front elevation view and a bottom plan view thereof, like elements having like numerals associated therewith in each case. FIGS. 10f and 10g are respectively a side elevation and a front elevation view of fourth anchor 90 as installed within base 10 of FIGS. 3a–3e,showing in Fig. 10f in particular the disposition of fourth shank 92 (indicated by the innermost pair of dashed lines) of fourth anchor 90 within anchor aperture 14 (indicated by the outermost pair of dashed lines) of base 10. It should be understood that as in the case of the previous anchor embodiments, the particular torque angle of fourth anchor 90 is arbitrarily selected, and may be varied for purposes of specific orthodontic applications when employed along with (i.e., adjacent to) anchors of the same or other types that likewise have selected torque angles.

FIG. 10h shows a perspective view of fourth anchor 90 as in FIG. 10a, but with first tipping spring 106 installed therein. First tipping spring 106 includes first spring shank 108 having a first spring head 110 at one end thereof and a spring lip 112 at the opposite end thereof. First spring head 110 further comprises spring coil 114, from which extends on one side thereof a first spring arm 116 that further includes first spring hook 118 at the distal end thereof. When first tipping spring 106 is placed within fourth anchor 90 by inserting the distal end of first spring shank 108 (at which end is located first spring lip 112) downwardly into spring slot 104, and when an arch wire also passes through fourth anchor 90, first spring head 110 may be installed such that first spring hook 118 engages that arch wire so as to exert an upward force thereon, and to exert such force on either side of fourth anchor 90 depending upon to which side thereof spring arm 116 extends.

Figure 10I:
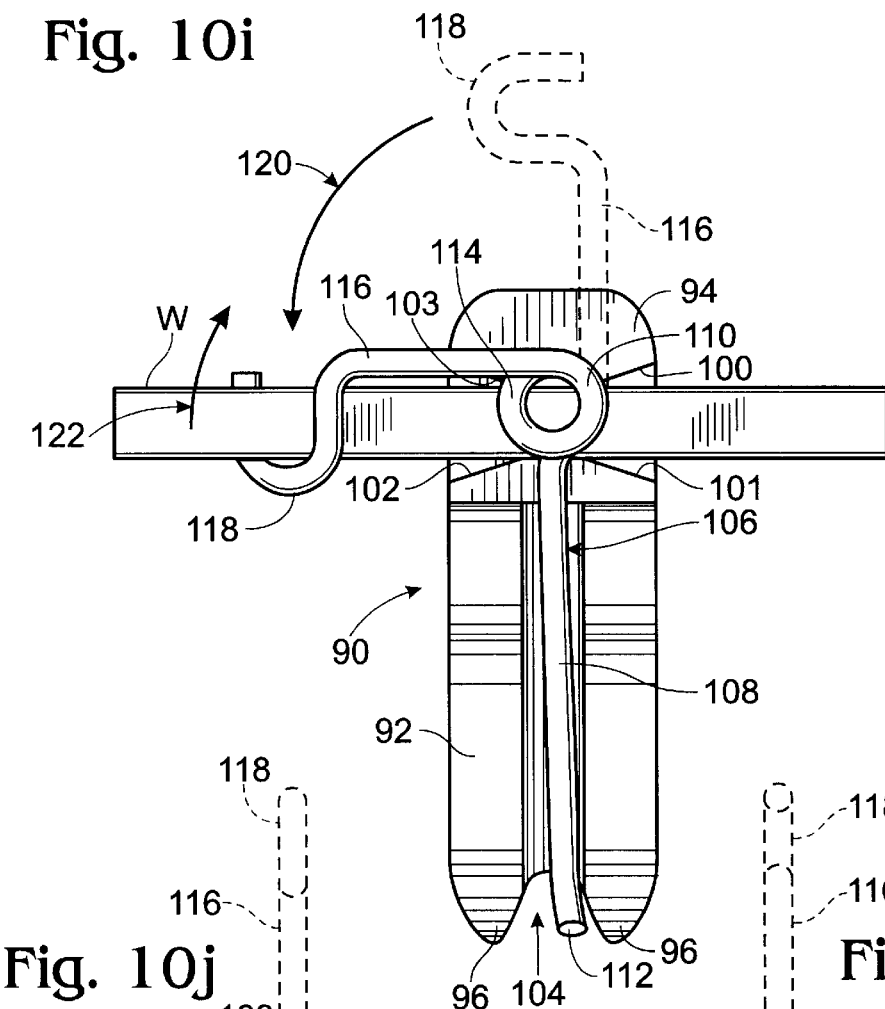
Figure 10J:
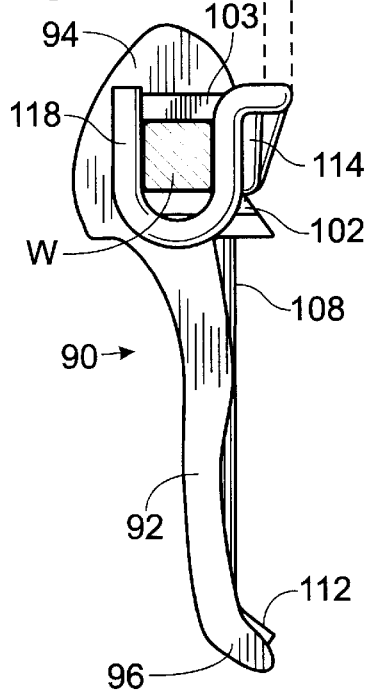
Figure 10K:
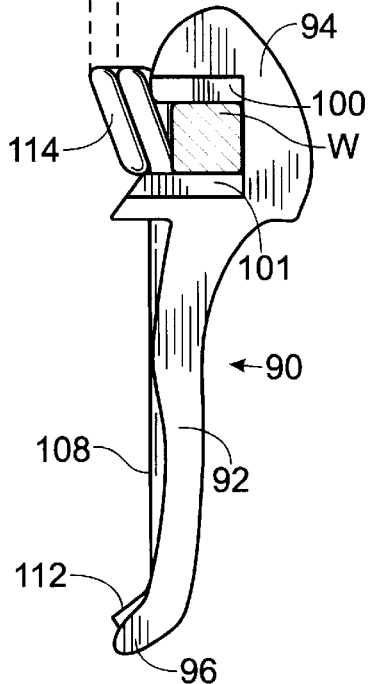
Figure 10L:
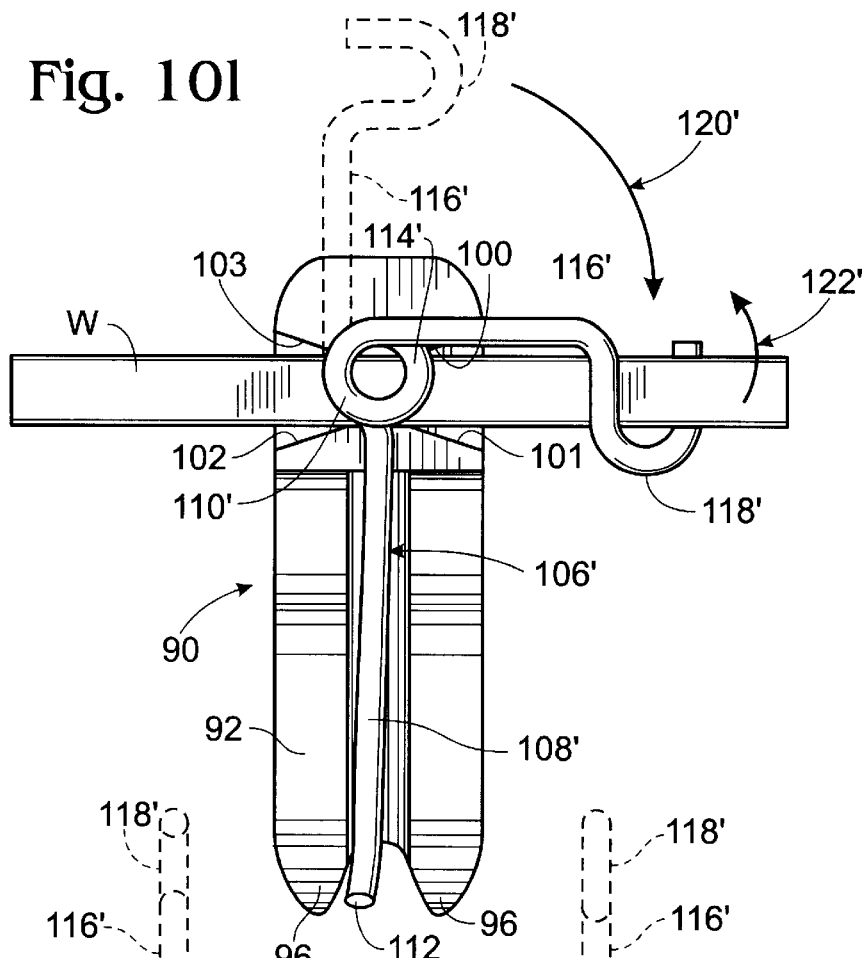
Figure 10M:
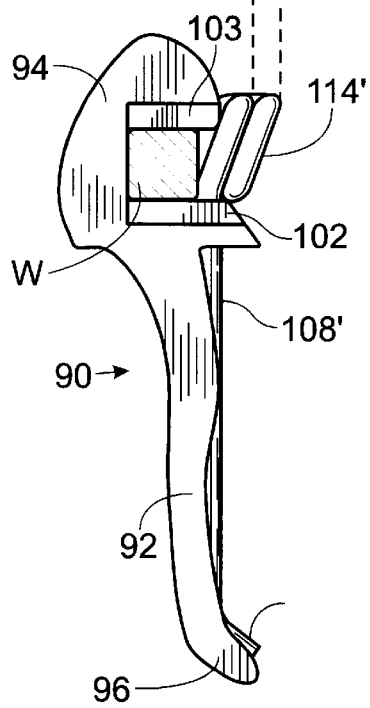
Figure 10N:
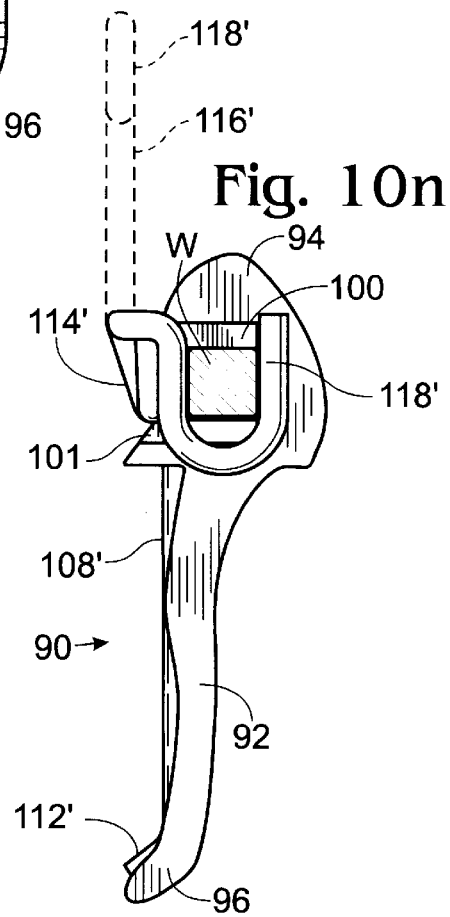

The aforesaid operation is shown in FIGS. 10i–10n. FIG. 10i is a front elevation view of fourth anchor 90 and first tipping spring 106 as shown in FIG. 10a, but with arch wire W also installed and showing the manner of operation of fourth head 94 and first tipping spring 106. The dashed form drawing of first spring arm 116 and first spring hook 118 shows the configuration realized when first tipping spring 106 is initially installed; the solid form drawing shows the disposition of first spring arm 116 and first spring hook 118 when applied to the arch wire W by way of manually bending first spring arm 116 as shown by arrow 120 and then hooking first spring hook 118 under wire W so as to exert on wire W the upward force on the left side thereof shown by arrow 122. FIGS. 10j–10k are respectively left and right side elevation views of the combination of fourth anchor 90, first tipping spring 106 and wire W as shown in FIG. 10i, other like elements again being shown by like numbers, and FIGS. 10l–10n are respectively comparable front elevation, left side elevation and right side elevation views of a case that employs second tipping spring 106' having second spring coil 114' from which second spring arm 116' extends rightwardly from second tipping spring 106', the other like elements again having like numerals associated therewith.

Figure 11A:
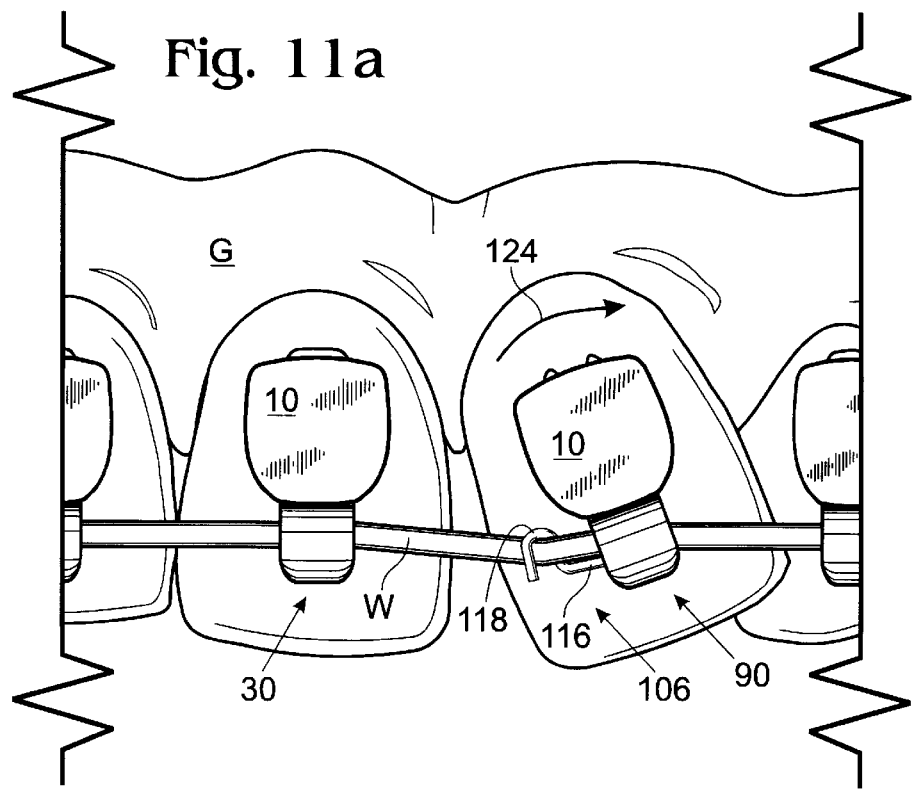
FIGS. 11a–11b illustrate uses of the anchor and base of FIGS. 10a–10n to the process of tilting a tooth in either the mesial or the distal direction.
Figure 11B:
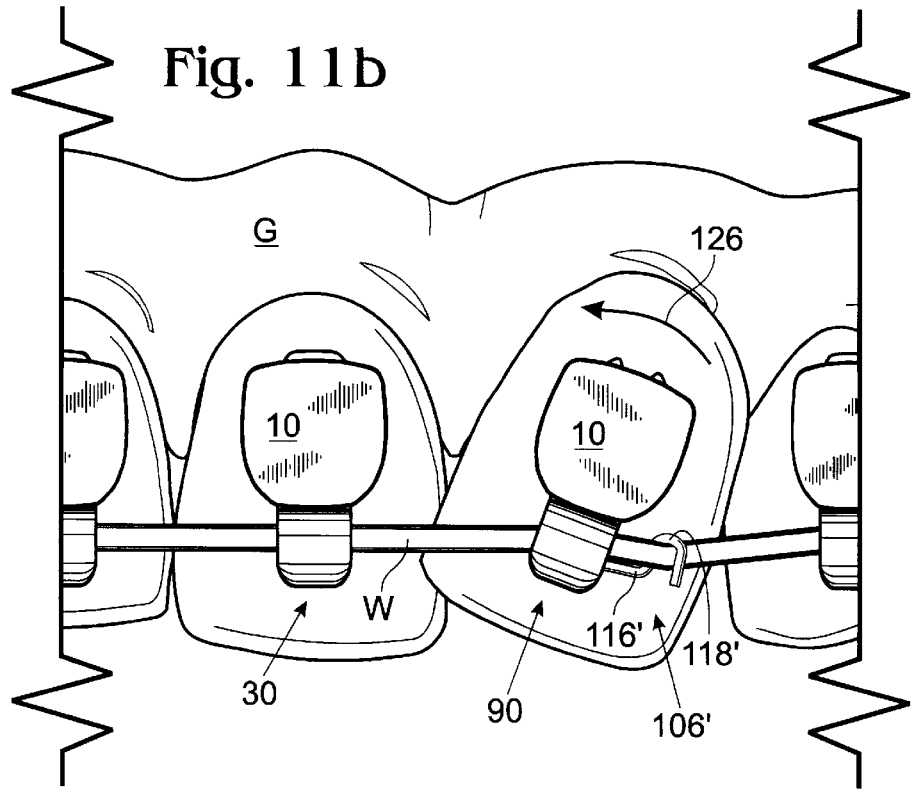

FIGS. 11a and 11b show the application of fourth anchor 90 and associated tipping springs 106 and 106' in exerting a tipping force on respective teeth as shown earlier in FIGS. 2a, 2b that require a tipping correction, like elements again having like numerals associated therewith in each case, and the tipping effect on the teeth so being corrected being shown respectively by arrows 124,126. Thus, in FIG. 11a, first tipping spring 106 in which first spring arm 116 extends leftwardly is used to permit hooking first hook 118 over wire W so as to cause the clockwise rotational force on the tooth shown by arrow 124. Similarly, FIG. 11b shows second tipping spring 106' that has second spring arm 116' extending rightwardly therefrom so as to permit second hook 118' to be hooked over wire W so as to cause the counter-clockwise rotational force on the tooth shown by arrow 126.

Figure 12A:
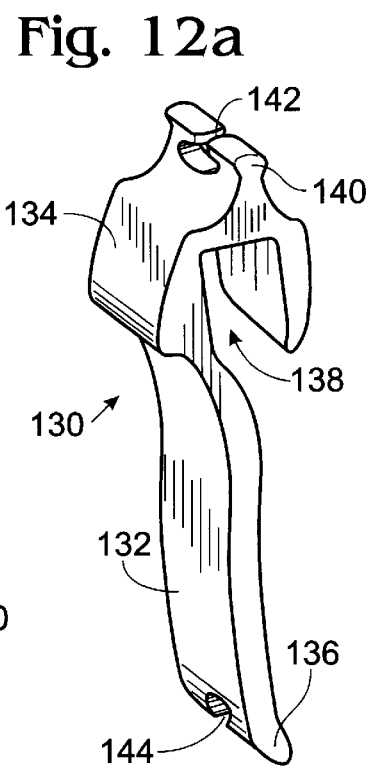
FIGS. 12a–12f show different views of a fifth embodiment of the invention, both separately and as installed in the base of FIGS. 3a–3f.
Figure 12B:
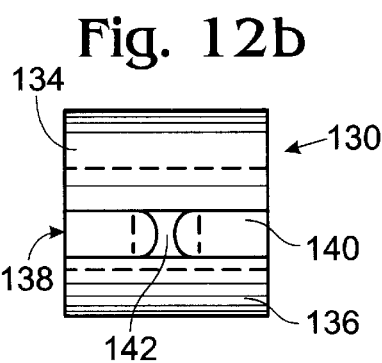
Figure 12C:
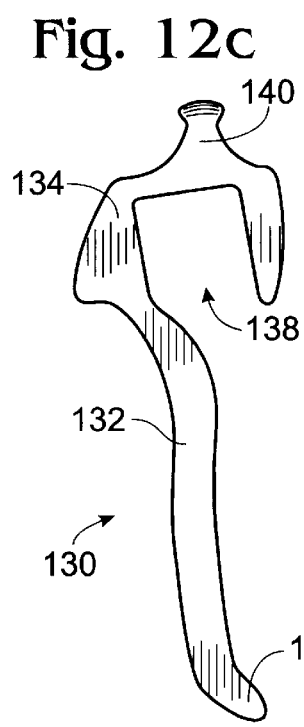
Figure 12D:
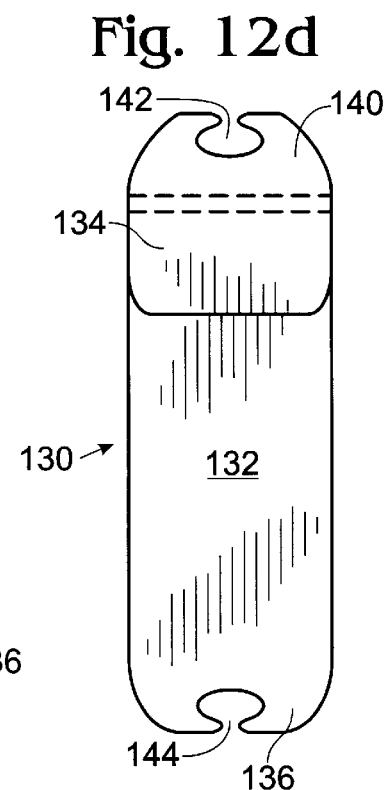
Figure 12F:
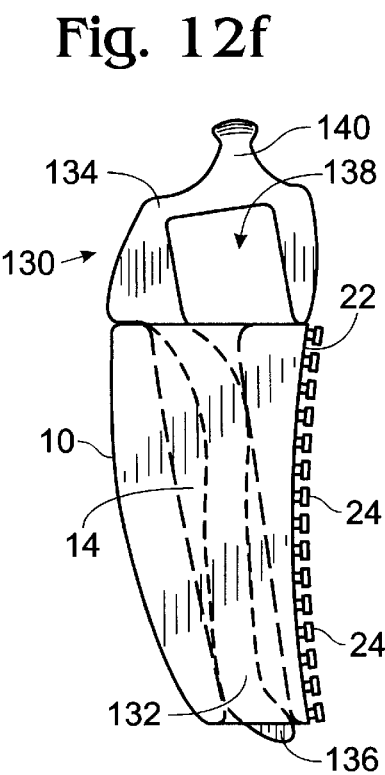
Figure 12E:
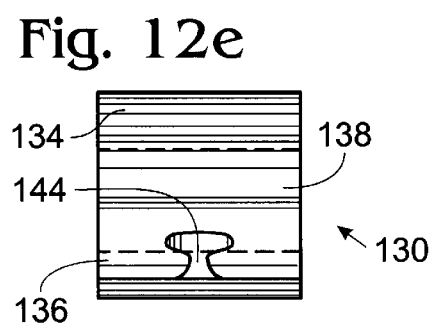

Yet another anchor type is shown in fifth anchor 130 of FIGS. 12a–12f. FIG. 12a is a perspective view of fifth anchor 130 that, similarly to the previous four embodiments, includes an elongate, undulating fifth shank 132, a fifth head 134 at one end thereof, and at the opposite end thereof a fifth lip 136. A fifth wire slot 138 passes transversely through fifth head 134. Fifth anchor 130 differs from the previous embodiments principally in that fifth head 134 further comprises a slot wall 140 disposed transversely across the top of fifth head 134, slot wall 140 further includes a first ovoid slot 142 disposed centrally and transversely thereto, and similarly fifth lip 136 includes a second ovoid slot 144 disposed centrally and transversely thereto. First and second ovoid slots 142, 144 provide another convenient means for making dual horizontal connections, as by a rubber band or module, from a tooth having a base 10 and fifth anchor 130 installed thereon, i.e., from the tooth so equipped to the two teeth horizontally adjacent thereto.

Figure 13:
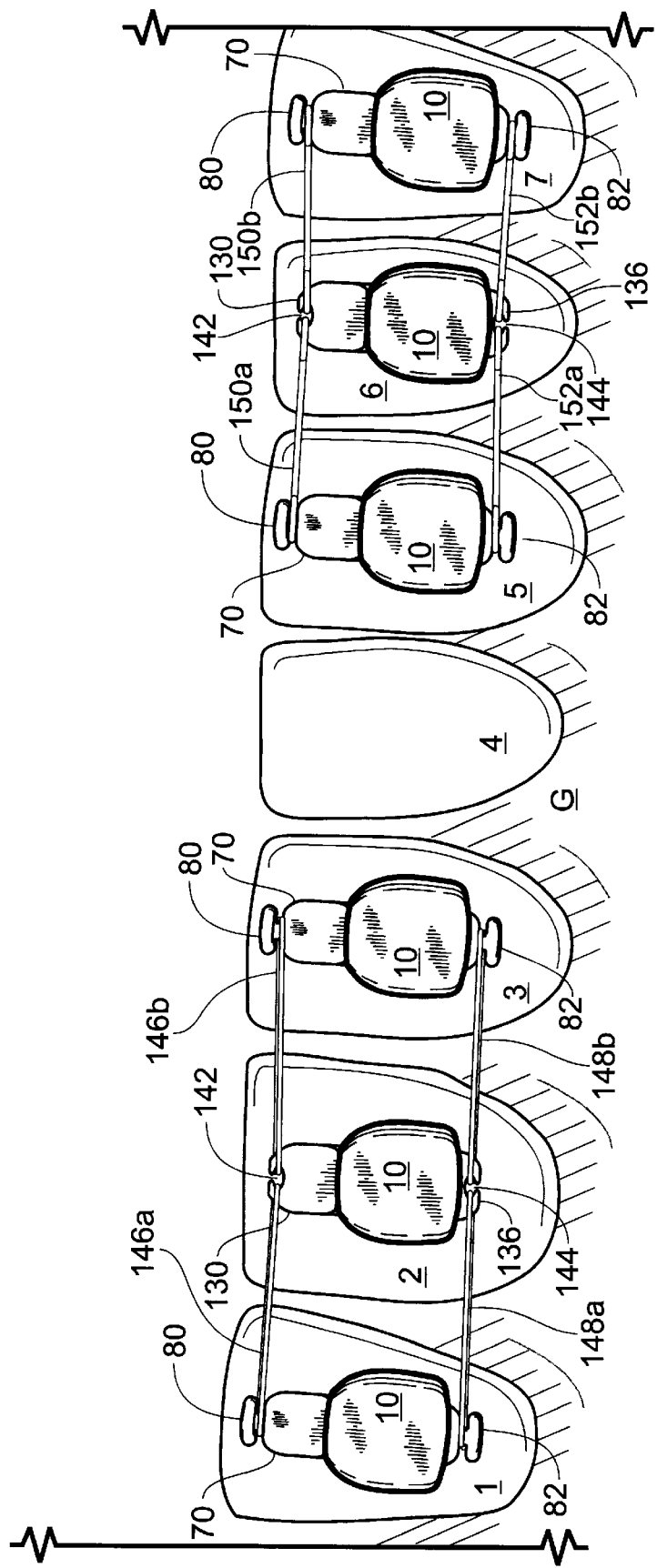
FIG. 13 illustrates uses of the anchor and base of FIGS. 12a–12f in making connection from a central tooth to the pairs of teeth on either side thereof.

FIG. 13 shows two instances of application of fifth anchor 130, specifically in a front elevation view of seven adjacent teeth 1–7, wherein the bases 10 that are installed on teeth 1, 3, 5, and 7 each have third anchors 70 installed therein, and the bases 10 that are installed on teeth 2 and 6 each have fifth anchors 130 installed therein. Central tooth 4 has no base or anchor installed thereon. To the leftward side of FIG. 13, pairs of rubber bands 146a, 146b are seen to extend respectively leftwardly and rightwardly from the first slot 142 of that fifth anchor 130 that is installed on tooth 2 to first anchor posts 80 of third anchors 70 installed on teeth 1, 3, and similarly as to rubber bands 148a, 148b extending respecively leftwardly and rightwardly from second slot 144 within fifth lip 136 thereof to second anchor posts 82 of third anchors 70 installed on teeth 1, 3. Similarly, to the rightward side of FIG. 13, pairs of modules 150a, 150b are seen to extend respectively leftwardly and rightwardly from the first slot 142 of that fifth anchor 130 that is installed on tooth 6 to first anchor posts 80 of third anchors 70 installed on teeth 5, 7, and similarly modules 152a, 152b extend respectively leftwardly and rightwardly from second slot 144 within fifth lip 136 thereof to second anchor posts 82 of third anchors 70 installed on teeth 5, 7.

It will be well understood by those of ordinary skill in the art that other arrangements and disposition of the aforesaid components, the descriptions of which are intended to be illustrative only and not limiting, may be made without departing from the spirit and scope of the invention. In particular, any of the aforesaid anchors to which an arch wire, or a rubber band or module or the like has been or is to be attached by tying or looping or the like, in lieu of providing a wire passing through a wire slot, would not then require that any such wire slot actually be present, inasmuch as for those particular purposes such an anchor would function in a manner entirely equivalent to such anchors as are shown and described herein that in fact include such a wire slot. Also, it will be understood that if so required, any or all of the several types of anchor and variations thereof in terms of torque angle or the like, and likewise the several means for interconnecting the same that are shown and described herein, may be "mixed and/or matched" in various combinations for particular orthodontic purposes.

I claim:

1. An orthodontic base for receiving an orthodontic anchor comprising:
    an elongate, tapered body having:
        opposite occlusal and gingival ends,
        a long dimension extending between said occlusal and gingival ends and sized to fit onto a surface of a tooth in parallel with a long axis of said tooth,
        a width dimension smaller than said long dimension and sized to fit within a width of a surface of said tooth,
        a depth dimension smaller than said width dimension, and one concave surface in a common plane of said long dimension and said width dimension; and
    an elongate rectangular orifice extending through said body in parallel with said long dimension of said body, said orifice having:
        an orifice width dimension extending parallel to said width dimension of said body, and
        a depth dimension smaller than said orifice width dimension and extending parallel to said depth dimension of said body,
    wherein said orifice depth dimension decreases in the occusal-gingival direction at predetermined, graduated rates so as to enable placement within said orifice of an undulated anchor, the subsequent removal of said anchor then requiring exertion in the gingival-occlusal direction of a predetermined removal force greater than a predetermined corrective force.

2. An orthodontic bracket comprising:
    an orthodontic base for receiving an orthodontic anchor comprising:

an elongate, tapered body having:
  opposite occlusal and gingival ends, a long dimension extending between said occiusal and gingival ends and sized to fit onto a surface of a tooth in parallel with a long axis of said tooth,
  a width dimension smaller than said long dimension and sized to fit within a width of a surface of said tooth,
  a depth dimension smaller than said width dimension, and one concave surface in a common plane of said long dimension and said width dimension; and
  an elongate rectangular orifice extending through said body in parallel with said long dimension of said body, said orifice having:
    an orifice width dimension extending parallel to said width dimension of said body, and
    a depth dimension smaller than said orifice width dimension and extending parallel to said depth dimension of said body,
  wherein said orifice depth dimension decreases in the occusal-gingival direction at predetermined, graduated rates so as to enable placement within said orifice of an undulated anchor, the subsequent removal of said anchor then requiring exertion in the gingival-occlusal direction of a predetermined removal force greater than a predetermined corrective force; and
an anchor having:
  an elongate, undulated shaft sized to pass lengthwise through said aperture in a force fit;
  a head disposed at a first end of said shaft further comprising a wire slot passing transversely therethrough and being open on a side thereof facing onto said base; and
  a lip disposed at a second end of said shaft opposite said first end and curved towards said open side of said wire slot.

3. The orthodontic bracket of claim 2 wherein said head further comprises an anchor post extending outwardly longitudinally from said head, said anchor post further comprising bilateral extensions therefrom of a sufficient length to come into contact with and exert pressure on an arch wire that passes through said wire slot on either side of said head when said head is rotated relative to said arch wire, whereby said arch wire is caused to exert a counter pressure against said extension to produce a rotational force about the long axis of said anchor.

4. The orthodontic bracket of claim 1 wherein said head further comprises pairs of anchor posts that respectively extend outwardly longitudinally from said head and said lip, said anchor posts each further comprising anchor plates of a broader dimension than said anchor posts disposed distally thereon, whereby a loop end of a connecting device may be held against one or both of said anchor posts between the head from which the respective anchor post extends and the corresponding anchor plate of said anchor post.

5. The orthodontic bracket of claim 1 wherein said anchor further comprises:
  a spring slot extending longitudinally therethrough on the side thereof facing onto said base;
  a tipping spring having a spring shank disposed within said spring slot and a spring head at the end of said spring shank proximal to said wire slot; wherein said spring head further comprises a spring coil and a spring arm extending outwardly longitudinally from said spring coil and including at the distal end thereof a spring hook, whereby a rotational force applied to said spring arm allows said spring arm to become disposed essentially parallel to an arch wire passing through said wire slot and said spring hook to become disposed about said arch wire in a hooking manner.

6. The orthodontic bracket of claim 2 wherein said anchor further comprises a slot wall disposed transversely across the distal end of said head, said slot wall further comprising a first ovoid slot disposed transversely therethrough, and said lip further comprises a second ovoid slot disposed transversely therethrough.

7. A method of carrying out orthodontic procedures on an arch of mammalian teeth, comprising the steps of:
  (a) providing an elongate base comprising a concavely curved surface sized to fit onto the labial surface of a tooth and an elongate aperture extending lengthwise through said base;
  (b) removably attaching a multiplicity of said elongate bases to labial surfaces of respective teeth disposed along said arch;
  (c) providing an elongate anchor comprising:
    an undulating shaft sized and shaped so as to require a force fit upon installation within said aperture, and
    a head near to a first end of said anchor, said head including a wire slot passing laterally therethrough;
  (d) installing by force fit within said multiplicity of elongate bases a corresponding multiplicity of said anchors such that each said wire slot thereof is disposed towards the occlusal end of each said tooth;
  (e) passing an arch wire sequentially through the corresponding multiplicity of wire slots; and
  (f) attaching opposite ends of said arch wire to respective teeth along said arch that are conveniently nearby to each of said opposite ends.

8. The method of claim 7 wherein step (c) thereof further comprises providing an elongate anchor comprising:
  an undulating shaft sized and shaped so as to require a force fit upon installation within said aperture;
  a head near to a first end of said anchor, said head including a wire slot passing laterally therethrough; and
  an anchor post extending outwardly lengthwise from said head, said anchor post further comprising bilateral extensions therefrom of a sufficient length to come into contact with and exert pressure on an arch wire that passes through said wire slot on either side of said head when said head is rotated relative to said arch wire, whereby said arch wire is caused to exert a counter pressure against said extension to produce a rotational force about a long axis of said anchor.

9. The method of claim 7 wherein step (c) thereof further comprises providing an elongate anchor comprising:
  an undulating shaft sized and shaped so as to require a force fit upon installation within said aperture;
  a head near to a first end of said anchor, said head including a wire slot passing laterally therethrough; and
  pairs of anchor posts that respectively extend outwardly longitudinally from said head and said lip, said anchor posts each further comprising anchor plates of a broader dimension than said anchor posts disposed distally thereon, whereby a loop end of a connecting device may be held against one or both of said anchor posts between the head from which the respective anchor post extends and the corresponding anchor plate of said anchor post.

10. The method of claim 7 wherein step (c) thereof further comprises providing an elongate anchor comprising:

an undulating shaft sized and shaped so as to require a force fit upon installation within said aperture;

a head near to a first end of said anchor, said head including a wire slot passing laterally therethrough;

a spring slot extending lengthwise through said shaft on a side thereof facing onto said base;

a tipping spring having a spring shank disposed within said spring slot and a spring head at the end of said spring shank proximal to said wire slot;

wherein said spring head further comprises a spring coil and a spring arm extending outwardly longitudinally from said spring coil and including at the distal end thereof a spring hook, whereby a rotational force applied to said spring arm allows said spring arm to become disposed essentially parallel to an arch wire passing through said wire slot and said spring hook to become disposed about said arch wire in a hooking manner.

11. The method of claim 7 wherein step (c) thereof further comprises providing an elongate anchor comprising:

an undulating shaft sized and shaped so as to require a force fit upon installation within said aperture;

a head near to a first end of said anchor, said head including a wire slot passing laterally therethrough; and a slot wall disposed transversely across the distal end of said head, said slot wall further comprising a first ovoid slot disposed transversely therethrough, and said lip further comprises a second ovoid slot disposed transversely therethrough.

* * * * *